(12) United States Patent
Lee et al.

(10) Patent No.: US 7,604,975 B2
(45) Date of Patent: Oct. 20, 2009

(54) GLYCOSYLATED LPXTGASES AND USES THEREOF

(75) Inventors: Sung Lee, New York, NY (US); Vijay Pancholi, Forest Hills, NY (US); Vincent A. Fischetti, West Hempstead, NY (US)

(73) Assignee: The Rockefeller University, New York, NY (US)

( * ) Notice: Subject to any disclaimer, the term of this patent is extended or adjusted under 35 U.S.C. 154(b) by 1013 days.

(21) Appl. No.: 10/677,097

(22) Filed: Oct. 1, 2003

(65) Prior Publication Data

US 2004/0146984 A1 Jul. 29, 2004

Related U.S. Application Data

(60) Provisional application No. 60/415,273, filed on Oct. 1, 2002.

(51) Int. Cl.
*C12N 9/48* (2006.01)
(52) U.S. Cl. .................................................... 435/212
(58) Field of Classification Search .................. 435/212
See application file for complete search history.

(56) References Cited

U.S. PATENT DOCUMENTS 5,968,763 A * 10/1999 Fischetti et al. ............... 435/23

OTHER PUBLICATIONS

Watanabe et al. "Properties and lytic action of the P2-2 enzyme capable or lysing cells of *Micrococcus radiodurans*" Agri. Biol. Chem. (1981) 45(5): 1215-1221.*
Hung Ton-That, et al, *PNAS*, 96, 12424-12429 (1999).
Mazmanian, et al., *Molecular Microbiology*, 40, 1049-1057 (2001).

* cited by examiner

*Primary Examiner*—Sandra Saucier
*Assistant Examiner*—Susan Hanley

(57) ABSTRACT

An endopeptidase is described which shows specificity for cleavage of a LPXTG (SEQ ID NO: 1) motif found in the cell membranes of gram positive bacteria, having an apparent molecular weight of 14,000 daltons, having a pH optimum of about 7.5 to 10, being salt sensitive, being heavily glycosylated, rich in alanine, lacking aromatic amino acids, having a $K_m$ of 0.26 mM and having a backbone comprised of about 30% unknown amino acids, and containing carbohydrates that are essential for its activity. Methods of use and pharmaceutical compositions of this inhibitor are described.

7 Claims, 19 Drawing Sheets

A B

Inhibitor Prevents M Protein Processing

Figure 19

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 3
<223> OTHER INFORMATION: Xaa = Any Amino Acid

<400> SEQUENCE: 1

Leu Pro Xaa Thr Gly
 1               5

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 2

Lys Arg Gln Leu Pro Ser Thr Gly Glu Thr Ala Asn Pro Phe Tyr
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Leu Pro Ser Thr Gly Glu
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Glu Gly Thr Ser Pro Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Thr Glu Pro Gly Ser Leu
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Thr Ala Asn Pro Phe Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Thr Gly Glu Thr Ala Asn Pro Phe Tyr
1               5
```

GLYCOSYLATED LPXTGASES AND USES THEREOF

CROSS-REFERENCE TO RELATED APPLICATIONS

The present application claims the benefit of priority to provisional application, Ser. No. 60/415,273, filed Oct. 1, 2002, which is hereby incorporated by reference in its entirety.

STATEMENT OF GOVERNMENT SUPPORT

The research leading to the present invention was supported in part by NIH Grant No. AI11822. The government may have certain rights in the present invention.

FIELD OF THE INVENTION

This invention relates to the identification, isolation and purification of a novel class of enzymes designated "LPXTGases" isolated from gram positive bacteria and the uses thereof. The invention further relates to the identification of inhibitors of these enzymes for treatment of infections caused by gram positive and gram negative bacteria, as well as screening methods for identification of novel inhibitors of LPXTGase, and pharmaceutical compositions comprising LPXTGase inhibitors for use in treatment of bacterial infections.

BACKGROUND OF THE INVENTION

A large group of cell surface proteins of gram-positive bacteria are covalently anchored through their C-termini to the cell wall peptidoglycan. Most of these proteins are essential for pathogenic bacteria to establish successful infection of host tissues, and hence they are considered virulence factors.

Functionally, these surface proteins may be divided into three major groups: viz., 1) those with adhesin or invasion function (Patti et al. (1994) Annu. Rev. Microbiol. 48:585-617; Courtney et al. (1994) Infect. Immun. 62: 4868-4873) those with antiphagocytic activities (Fischetti et al. (1995) Infect. Immun. 63:149-153; Gigli et al. (1979) Proc. Natl. Acad. Sci. U.S.A. 76: 6596-6600), and 3) those that are enzymes that degrade surface components of host cells, thereby facilitating spread, and enzymes that hydrolyze large molecules in the surroundings into utilizable nutrients (Igarashi et al. (1995) Microbiol. Immunol. 39:853-860; Berry et al. (1996) J. Bacteriol. 178:4854-4860).

A striking feature of all these functionally and structurally diverse surface proteins is that they all possess a carboxy-terminal LPXTG sequence (Fischetti et al. (1990) Molec. Microbiol. 4: 1603-1605) which is cleaved during surface translocation at the septum (Mazmanian et al. (1999) Science 285: 760-762), resulting in a covalent linkage to cell wall peptidoglycan. In all cases, the genes for these proteins contain additional nucleotide sequences following that which encodes the LPXTG. These additional sequences encode a stretch of hydrophobic amino acids and positively charged C-terminal amino acids. Pancholi and Fischetti observed that the hydrophobic and positively charged amino acid sequences are missing in the cell wall-linked M protein, indicating that the precursor of M protein was cleaved at a site within or immediately C-terminal to the LPXTG sequence (Pancholi et al. (1988) J. Bacteriol. 170: 2618-2624). These findings strongly indicated that surface proteins become anchored to cell wall by a common mechanism (Fischetti et al. (1990) Molec. Microbiol. 4: 1603-1605).

Subsequently, it was also shown that deletion of either the LPXTG, or hydrophobic amino acid sequence or charged terminal amino acid from the precursor of protein A of S. aureus results in failure of protein A anchoring to the cell wall (Schneewind et al. (1992) Cell 70: 267-281), indicating that these sequences were essential for cell wall-anchoring process of these proteins. Collectively, these sequences are considered to be a cell wall sorting signal, which have now been shown to be present in over 100 surface proteins of gram-positive bacteria (Navarre et al. (1999) Microbiol. Molec. Biol. Reviews 63: 174-229; Pallen et al. (2001) Trends Microbiol. 9: 97-102).

Schneewind and colleagues have shown that the peptide bond between threonine and glycine of the LPXTG sequence of protein A becomes cleaved by an enzyme termed sortase, after which the carboxy-terminus of threonine becomes covalently attached to the amino group of one of the glycines of the pentaglycine cross bridge of the S. aureus cell wall (Schneewind et al. (1995) Science 268: 103-106). Recently, they have shown that S. aureus mutants defective in the anchoring of surface proteins to the cell wall carry a mutation in srt gene (Mazmanian et al. (1999) Science 285: 760-762). Subsequently they cloned the srt A gene in E. coli, and purified recombinant sortase. In vitro, the purified sortase cleaved the LPXTG sequence after threonine (Ton-That et al. (1999) Proc. Natl. Acad. Sci. U.S.A. 96: 12424-12429), and also covalently attached the surface protein with C-terminal LPXT to a triglycine substrate (Ton-That et al. (2001) J. Biol. Chem.). These results indicate that sortase possesses two functions, a specific endopeptidase and a transpeptidase. In addition, they showed that S. aureus mutants lacking sortase are unable to display surface proteins and are defective in establishing infection (Mazmanian et al. (2000) PNAS 97:5510-5515). An analysis of the genome of several gram-positive bacteria revealed that there are more than one sortase gene per bacterial genome (Pallen et al. (2001) Trends Microbiol. 9: 97-102).

SUMMARY OF THE INVENTION

The first aspect of the invention provides for the identification of a novel class of glycosylated enzymes designated "LPXTGases" isolated from procaryotes, which are assembled by a number of biosynthetic steps independent from genetic synthesis. This class of enzymes is specific for cleavage of the conserved Leu Pro Xaa Thr Gly ("LPXTG") (SEQ ID NO:1) sequence found in surface proteins of gram positive bacteria, and may play a role in the ability of the bacteria to bind to the host cell, thereby enhancing the spread of infection. The polypeptide backbone of the LPXTGases may be assembled enzymatically as opposed to ribosomally, from amino acids. Carbohydrates are synthesized separately and subsequently linked to the polypeptide backbone.

In a more specific embodiment, the invention provides for the identification of a novel, heavily glycosylated "LPXTGase", enzyme, which is about 14 kDa in size, has no aromatic amino acids, is rich in alanine and is composed of 30% uncommon amino acids, suggesting a non-ribosomal construction. Out of the 24 alanine residues identified, about six or seven exist in the D form rather than the L form. The scientific evidence for the physical and biochemical properties associated with this novel enzyme is provided below. Based on the fact that this is the first enzyme of its kind to be identified in prokaryotes, this may lead the way in the identification of other similarly synthesized critical enzymes that may be targets for antibiotic development.

The second aspect of the invention provides for methods of isolation and purification of inhibitors of this class of LPXTGase enzymes. Certain methods for the isolation, purification and characterization of such inhibitors are provided below. In one embodiment, the method for isolation and purification of one such inhibitor of LPXTGase activity includes isolation from Streptococcal membrane extracts using DEAE cellulose chromatographic techniques, followed by further purification through thin layer silica gel chromatography. The methods provided herein for the isolation and purification of LPXTGase inhibitors may serve as the basis for identification of other molecules possessing similar inhibitory activity.

Thus, a third aspect of the invention provides for identification of small molecule inhibitors of LPXTGase that may interfere with either the assembly of the enzyme, or the actual inhibition of enzyme activity. In one specific embodiment, a method for identifying and testing the effect of an inhibitor on enzyme activity is provided herein and includes attachment of an $^{125}$I-labeled LPXTG-containing substrate to glass beads, followed by incubation of the beads with enzyme in the presence or absence of the potential inhibitor. A decrease of released peptide fragment in the presence of the inhibitor is evidence of enzyme inhibition.

A fourth aspect of the invention provides for methods of screening for novel LPXTGase inhibitors in a cell-free assay system. In one embodiment, inhibitors of LPXTGase activity are identified using radioactively labeled beads containing an LPXTGase substrate, followed by incubation of these beads with the enzyme plus or minus the potential inhibitor. Release of radioactivity into the supernatant is used as a readout of enzyme activity or inhibition thereof. Although this method can be used for screening for novel inhibitors, adaptation of this method for use in high-throughput screening is envisioned. For example, Fluorescence Quenching Assays may be used to identify LPXTGase inhibitors. Using this methodology, a peptide substrate is designed such that a fluorescent dye and a quencher would be proximal to each other. In the absence of an inhibitor of LPXTGase, the enzyme is free to cleave the peptide substrate resulting in an increase in release of the fluorescent dye. In the presence of an inhibitor of LPXTGase, there is no cleavage of the substrate, and thus no release of fluorescent dye. Although the example provided in the present application with one specific inhibitor provides sufficient proof of the efficacy of such inhibitors, the scope of such inhibitors envisioned extends beyond the example provided.

A fifth aspect of the invention provides for the use of LPXTGase inhibitors in prevention of bacterial cell growth in vitro and in vivo. Evidence for the effects of such LPXTGase inhibitors on inhibition of bacterial cell growth are demonstrated herein. One embodiment of the invention features broad spectrum use of the inhibitors to prevent growth of gram positive and gram negative bacteria, as well as inhibition of growth of other strains of bacteria, including mycobacteria. The inhibitors of LPXTGase activity are envisioned to be small molecule inhibitors, antibodies, antibody fragments or mimics thereof.

A sixth aspect of the invention provides for pharmaceutical compositions comprising purified LPXTGase inhibitors for therapeutic use in treatment of bacterial infections. One embodiment features treatment of a wide range of infections including those caused by gram positive, gram negative or mycobacterial infection with pharmaceutical compositions containing acceptable carriers and excipients. Moreover, a further embodiment may include a pharmaceutical composition designed for use in topical treatment of bacterial infections. Another embodiment may include a pharmaceutical composition designed for use in treatment of systemic infections, or infections that are non-responsive to other antibiotic modalities.

Other advantages of the present invention will become apparent from the ensuing detailed description taken in conjunction with the following illustrative drawings.

BRIEF DESCRIPTION OF THE DRAWINGS

FIG. 19 shows the molecular weight profile on electrophoretic gels of the M protein isolated from Streptococcus grown in the presence or absence of the LPXTGase inhibitor. Organisms grown in the presence of the inhibitor had a larger M protein, indicating that the LPXTGase was blocked from cleaving the C-terminal region of the molecule.

DETAILED DESCRIPTION

Figure 1:
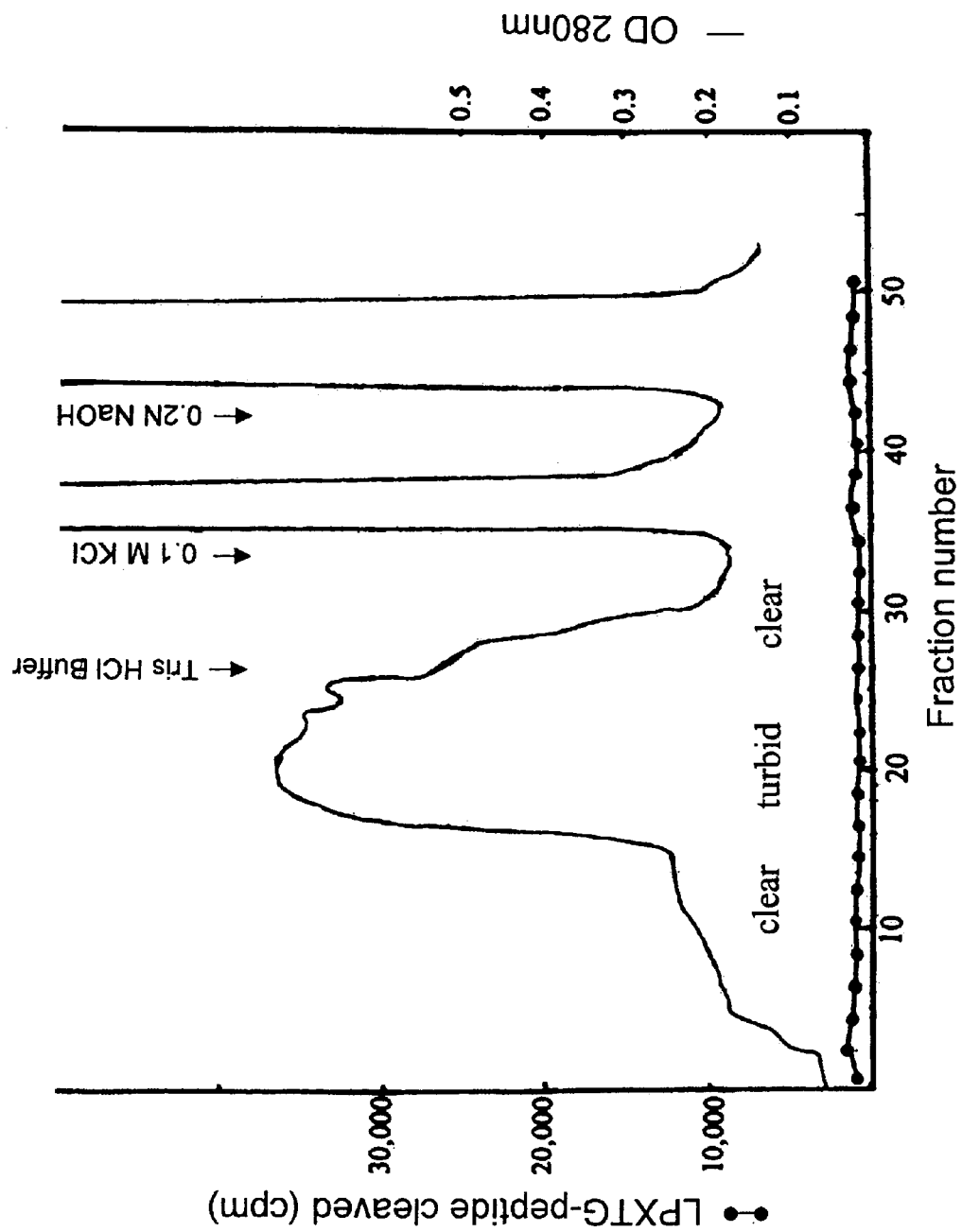
FIG. 1 shows DEAE-cellulose chromatography of the cytosol fraction from *Streptococcus pyogenes*. The cytosol fraction containing membrane vesicles was chromatographed on a DEAE cellulose column. Aliquots (10 µl) of fractions were assayed for cleavage activity of glass bead-bound $^{125}$I-labeled LPXTG-containing peptide. Clear and turbid describe the appearance of the solution eluting from the column in the fractions.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Definitions

"Treatment" refers to the administration of medicine or the performance of medical procedures with respect to a patient, for either prophylaxis (prevention) or to cure the infirmity or malady in the instance where the patient is afflicted.

The term "antibody" as used herein includes intact molecules as well as fragments thereof, such as Fab and F(ab')$_2$, which are capable of binding the epitopic determinant. Antibodies that bind LPXTGase can be prepared using intact polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit).

A "therapeutically effective amount" is an amount sufficient to decrease or prevent the symptoms associated with the bacterial infection associated with the presence of LPXTGase activity in the bacteria.

"Unknown amino acids" are those that are not included in the standard 20 known amino acids. The standard known amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The unknown amino acids may include for example, the D-form of a known amino acid or derivatives of such amino acids, such as for example L-ornithine, L-homocysteine, L-homoserine, L-citrulline, 3-sulfino-L-alanine, N-(L-arginino) succinate, 3,4-dihydroxy-L-phenylalanine, 3-iodo-L-tyrosine, 3,5-diiodo-L-tyrosine, triiodothyronine, L-thyroxine, L-selenocysteine, beta-alanine, N-(L-arginino)taurine, 4-aminobutylate, (R,S)-3-amino-2-methylpropanoate, D-alanine, D-valine, D-leucine, D-isoleucine, D-aspartate, D-asparagine, D-glutamate, D-glutamine, D-serine, D-threonine, D-methionine, D-cysteine, D-lysine, D-arginine, D-histidine, D-proline, D-phenylalanine, D-tyrosine, and D-tryptophan. The molecule described in the present application may have some of these unusual amino acids, as well as other unusual amino acid derivatives.

General Description

A novel enzyme, designated "LPXTGase" has been identified and isolated from cell membrane extracts of *Streptococcus pyogenes*. This enzyme possesses endopeptidase activity and cleaves a conserved LPXTG (SEQ ID NO:1) motif present in surface proteins on gram positive bacteria. LPXTGase, which is about 14,000 Da in size, is heavily glycosylated, and its amino acid composition and sequence analysis reveal the absence of aromatic amino acids. Moreover, LPXTGase cleaves after glutamic acid, does not have cysteine or methionine, is totally insensitive to sulfhydryl agents and its activity is inhibited by hydroxylamine. The carbohydrate moiety in LPXTGase appears to be essential for enzyme activity. No precedent for a glycosylated enzyme existing in prokaryotes is known to the inventors. Moreover, the core protein of the LPXTGase is extremely hydrophobic, rich in alanine and about 30% of the enzyme is made up of uncommon amino acids, suggesting a non-ribosomal construction. The LPXTGase enzyme is salt sensitive and probably reflects an intimate association of the enzyme with the hydrophobic environment of the membrane. A similar enzyme, found in the membrane extract of *Staphylococcus aureus*, suggests that this unusual molecule may be common among gram positive bacteria.

The novel enzyme described herein plays an important role in cleavage of the LPXTG motif necessary for the anchoring of surface proteins, thus enabling anchoring of bacterial surface proteins to cell wall peptidoglycan, thereby enabling more efficient binding of the bacteria to their respective host cells and concurrent increase in establishment of infection in their host. The findings in the present application suggest that a search for inhibitors of this enzyme may prove to be a useful strategy for identifying a new class of antimicrobial agents and treatment modalities.

Moreover, the invention provides for the identification, isolation and purification of a novel class of glycosylated enzymes, designated "LPXTGases", which are isolated from procaryotes, and at least part of which are assembled by a number of biosynthetic steps independent from genetic synthesis. Wherein the level of glycosylation is defined relative to a maximum of 100%, the enzyme may be glycosylated from 0 to 100%, more specifically from 20 to 80%, and even more specifically from 40 to 60%.

In a specific embodiment, one LPXTGase enzyme was isolated from a membrane extract and also from cytosol fraction, which is effused with membrane fragments, of *Streptococcus pyogenes* using the protocol outlined in Examples 1 and 2, which includes chromatography of the cytosol fraction first through DEAE-cellulose, followed by concentration of the fall-through fractions by means of ultrafiltration and further chromatography through a Sephadex G50 column. Activity of the enzyme was also monitored by measuring cleavage of an LPXTG-peptide, labeled with $^{125}$I-tyrosine, as shown in Example 4. Using this protocol, the LPXTGase enzyme proved to be about 14 kDa in size. Examples 7 and 8 show that the enzyme is heavily glycosylated, and Example 10 shows that the enzyme contains unusual amino acids, a nonribosomal construction. In addition, Table 2 shows that the enzyme is rich in alanine and contains no aromatic amino acids, nor sulfur-containing amino acids.

Another aspect of the invention provides for identification of small molecule inhibitors of LPXTGase that may interfere with either the assembly of the enzyme, or may actually inhibit enzyme activity. In one specific embodiment, a method for identifying and testing the effect of an inhibitor on enzyme activity is provided herein and includes attachment of an $^{125}$I-labeled LPXTG-containing substrate to glass beads, followed by incubation of the beads with enzyme in the presence or absence of the potential inhibitor. Release of radioactivity following a suitable incubation period is evidence of enzyme activity with a decrease in release of radioactivity being evidence of enzyme inhibition. Although the example provided in the present application with one specific inhibitor provides sufficient proof of the efficacy of such inhibitors, the scope of such inhibitors envisioned extends beyond the example provided.

Screening Assays

The invention provides methods for identifying agents (e.g., chemical compounds, carbohydrates, proteins, peptides, antibodies or nucleotides) that have an inhibitory effect on the assembly of LPXTGase or on the activity of LPXTGase. The invention also provides methods of identifying agents, candidate compounds or test compounds that specifically bind to LPXTGase. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No.5,807,683, each of which is incorporated herein in its entirety by reference).

In one embodiment, agents that interact with (i.e., bind to) LPXTGase or a polypeptide or fragment (e.g. a functionally active fragment), are identified in a cell-based assay system. In accordance with this embodiment, cells expressing LPXTGase comprising an LPXTGase peptide or polypeptide, a fragment thereof, are contacted with a candidate compound or a control compound and the ability of the candidate compound to interact with LPXTGase is determined. If desired, this assay may be used to screen a plurality (e.g., a library) of candidate compounds. The cell, for example, can be of prokaryotic origin (e.g., S. pyogenes or S. aureus), and may contain the LPXTGase peptide or polypeptide, fragment, or related polypeptide thereof. In some embodiments, the LPXTGase or LPXTGase polypeptide, fragment, or related polypeptide thereof or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a LPXTGase and a candidate compound. The ability of the candidate compound to interact directly or indirectly with the LPXTGase can be determined by methods known to those of skill in the art. For example, the interaction can be determined by flow cytometry, a scintillation assay, immunoprecipitation or western blot analysis.

In another embodiment, agents interact with (i.e., bind to) LPXTGase in a cell-free assay system. In accordance with this embodiment, LPXTGase is contacted with a candidate compound or a control compound and the ability of the candidate compound to interact with the LPXTGase is determined. If desired, this assay may be used to screen a plurality (e.g. a library) of candidate compounds. In one embodiment, the LPXTGase is first immobilized, by, for example, contacting the LPXTGase with an immobilized antibody which specifically recognizes and binds it, or by contacting a purified preparation of the LPXTGase with a surface designed to bind proteins. The LPXTGase may be partially or completely purified (e.g., partially or completely free of other polypeptides) or part of a cell lysate. In another embodiment, inhibitors of LPXTGase activity are identified using radioactively labeled beads containing an LPXTGase substrate, followed by incubation of these beads with the enzyme plus or minus the potential inhibitor. Release of radioactivity into the supernatant is used as a readout of enzyme activity or inhibition thereof. Although this method can be used for screening for novel inhibitors, adaptation of this method for use in high-throughput screening is envisioned. Included in this aspect may be the use of an enzyme-linked immunoassay or radio-immunoassay format to establish effects of potential inhibitors on enzyme activity. The ability of the candidate compound to interact with the LPXTGase can be determined by methods known to those of skill in the art.

In another embodiment, a cell-based assay system is used to identify agents that bind to or modulate the activity of the LPXTGase, or a biologically active portion thereof. In a primary screen, a plurality (e.g., a library) of compounds are contacted with cells that naturally express LPXTGase in order to identify compounds that modulate the assembly of the LPXTGase. The ability of the candidate compound to modulate the formation of the LPXTGase can be determined by methods known to those of skill in the art, including without limitation, flow cytometry, a scintillation assay, immunoprecipitation and western blot analysis.

In another embodiment, agents that competitively interact with (i.e., bind to) LPXTGase are identified in a competitive binding assay. In accordance with this embodiment, cells containing LPXTGase are contacted with a candidate compound and a compound known to interact with the LPXTGase or prevent the assembly of LPXTGase; the ability of the candidate compound to competitively interact with the LPXTGase or to competitively prevent assembly of the LPXTGase is then determined. Alternatively, agents that competitively interact with (i.e., bind to) LPXTGase or competitively prevent the assembly of LPXTGase are identified in a cell-free assay system by contacting the LPXTGase or components able to form an active LPXTGase with a candidate compound and a compound known to interact with or prevent the assembly of LPXTGase. As stated above, the ability of the candidate compound to interact with LPXTGase or prevent the assembly of an active LPXTGase can be determined by methods known to those of skill in the art. These assays, whether cell-based or cell-free, can be used to screen a plurality (e.g., a library) of candidate compounds.

In another embodiment, agents that modulate (i.e., up-regulate or down-regulate) the assembly of LPXTGase are identified by contacting cells (e.g., cells of prokaryotic origin) containing the components capable of forming an enzymatically active LPXTGase with a candidate compound or a control compound (e.g., phosphate buffered saline (PBS)) and determining the assembly or activity of the LPXTGase. The level of LPXTGase assembly or LPXTGase activity in the presence of the candidate compound is compared to the level of assembly or activity in the absence of the candidate compound (e.g., in the presence of a control compound). The candidate compound can then be identified as a modulator of the formation or assembly of the LPXTGase based on this comparison. For example, when presence of an enzymatically active LPXTGase is significantly greater in the presence of the candidate compound than in its absence, the candidate compound is identified as a stimulator of LPXTGase formation and/or an enhancer of LPXTGase activity. Alternatively, when presence of an enzymatically active LPXTGase is significantly less in the presence of the candidate compound than in its absence, the candidate compound is identified as an inhibitor of LPXTGase formation or assembly and/or inhibitor of LPXTGase activity.

In another embodiment, agents that modulate the activity of an enzymatically active LPXTGase molecule are identified by contacting a preparation containing the LPXTGase enzyme, or cells (e.g., prokaryotic) forming an enzymatically active LPXTGase with a test compound or a control compound and determining the ability of the test compound to modulate (e.g., stimulate or inhibit) the activity of the LPXTGase. The activity of the LPXTGase can be assessed in a number of ways, known to those skilled in the art.

In another embodiment, agents that modulate (i.e., up-regulate or down-regulate) the assembly, activity or both, of LPXTGase are identified in an animal model. Examples of suitable animals include, but are not limited to, mice, rats, rabbits, monkeys, guinea pigs, dogs and cats. Preferably, the animal used represents a model of an LPXTGase-associated disease or infection, such as that caused by bacteria harboring the LPXTGase enzyme. Examples of such infections may be those caused by Streptococcus, Staphylococcus, or Mycobacteria.

In accordance with this embodiment, the test compound or a control compound is administered (e.g., topically, orally, rectally or parenterally such as intraperitoneally or intravenously) to a suitable animal and the effect on the assembly, activity or both assembly and activity of the LPXTGase is determined, or the effect on an LPXTGase-bearing target cell is determined. Changes in the activity of LPXTGase can be assessed by any suitable method described above, based on the present description.

This invention further provides novel agents identified by the above-described screening assays and uses thereof for treatments as described herein.

Therapeutic Uses of the Invention

Another aspect of the invention provides for the use of LPXTGase inhibitors in prevention of bacterial cell growth in vitro and in vivo. Evidence for the effects of such LPXTGase inhibitors on inhibition of bacterial cell growth are demonstrated herein. One embodiment of the invention features broad spectrum use of the inhibitors to prevent growth of gram positive and gram negative bacteria, as well as inhibition of growth of other strains of bacteria, including mycobacteria. The inhibitors of LPXTGase activity are envisioned to be small molecule inhibitors, peptides, polypeptides, antibodies, antibody fragments or mimics thereof.

The invention provides for treatment or prevention of various diseases and disorders by administration of a therapeutic agent. Such agents include but are not limited to: agents which prevent formation or assembly of the LPXTGase enzyme, agents which modulate the activity of LPXTGase, agents able to act as antagonists of LPXTGase, and related analogs, derivatives, and fragments thereof. Such antagonists may include small molecule inhibitors or antibodies to LPXTGase.

In one embodiment wherein inhibition of the LPXTGase is desirable, one or more inhibitors, each specifically binding to the LPXTGase, are administered alone or in combination with one or more additional therapeutic compounds or treatments. In a preferred embodiment, an LPXTGase inhibitor is administered to a human subject for therapy (e.g. to ameliorate symptoms or to retard onset or progression) of bacterial infections.

Assays for Therapeutic Compounds

The present invention also provides for assays for use in discovery of pharmaceutical products in order to identify or verify the efficacy of compounds for treatment or prevention of LPXTGase-mediated infectious diseases. In one embodiment, agents can be assayed for their ability to inhibit bacterial growth in vitro or in vivo. Compounds able to reduce LPXTGase activity in vitro can be further tested for antibacterial activity in experimental animal models of infectious disease and can be used as lead compounds for further drug discovery, or used therapeutically.

In various embodiments, in vitro assays can be carried out with bacterial cells that harbor the LPXTGase enzyme and that are representative of the bacterial cell type involved in a subject's disease, to determine if a compound has a desired effect upon such bacterial cell types. In one embodiment, the cells are Streptococcus, Staphylococcus, Mycobacterium, or gram negative bacterial cells.

Compounds for use in therapy can be tested in suitable animal model systems prior to testing in humans, including but not limited to rats, mice, chicken, cows, monkeys, rabbits, etc. For in vivo testing, prior to administration to humans, any animal model system known in the art may be used. In one embodiment, test compounds that modulate the formation, assembly or activity of enzymatically active LPXTGase are identified in non-human animals (e.g., mice, rats, monkeys, rabbits, and guinea pigs), preferably non-human animal models for LPXTGase-associated infectious diseases. In accordance with this embodiment, a test compound or a control compound is administered to the animals, and the effect of the test compound on LPXTGase levels or activity is determined in the bacterial organism obtained from the infected animal. A test compound that alters the level or activity of LPXTGase can be identified by comparing the level of the selected LPXTGase in a bacterial culture obtained from an animal or group of animals treated with a test compound with the level of the LPXTGase in a bacterial culture obtained from an animal or group of animals treated with a control compound.

In yet another embodiment, test compounds that modulate the level or activity of LPXTGase are identified in human subjects having an infection associated with bacteria that contain the LPXTGase enzyme. In accordance with this embodiment, a test compound or a control compound is administered to the human subject, and the effect of a test compound on either reduction in spread of the microbial infection, elimination of the bacterial infection or amelioration of symptoms associated with the infection is determined by methods known in the art.

Therapeutic and Prophylactic Compositions and Their Use

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; any suitable method known to the art may be used.

Another aspect of the invention provides for pharmaceutical compositions comprising purified LPXTGase inhibitors for therapeutic use in treatment of bacterial infections. One embodiment features treatment of a wide range of infections including those caused by gram positive, gram negative or mycobacterial infection with pharmaceutical compositions containing acceptable carriers and excipients. Moreover, a further embodiment may include a pharmaceutical composition designed for use in topical treatment of bacterial infections. Another embodiment may include a pharmaceutical composition designed for use in treatment of systemic infections, or infections that are non-responsive to other antibiotic modalities.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of infectious diseases wherein the bacteria contain the LPXTGase enzyme can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872-10876). In one embodiment, administration can be by direct injection by aerosol inhaler.

In another embodiment, the inhibitor compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the inhibitor compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

EXAMPLES

The following examples are put forth so as to provide those of ordinary skill in the art with a complete disclosure and description of how to isolate and use the novel class of enzymes described herein, and to provide a suitable means for identifying and assaying appropriate inhibitors of this class of enzyme and development of pharmaceutical compositions for therapeutic use, and are not intended to limit the scope of Purification of LPXTGase: To about 1.8 liter of the cytosol fraction, Brij-35 was added to a final concentration of 0.1%, and the fraction was applied to a DEAE-cellulose column (16 cm×4.3 cm) equilibrated with 20 mM Tris-HCl buffer, pH 6.8. About 500 ml of clear solution absorbing UV at 280 nm eluted first, followed by turbid UV absorbing solution. After all the applied cytosol fraction entered the column, the column was washed with 20 mM Tris-HCl buffer, pH 7.6, containing 0.1 % Brij 35. The wash step eluted additional turbid solution, and then eluted a clear UV-absorbing solution. Generally, 500 ml of wash buffer was required until UV absorbance returned to baseline. The column was then eluted with 0.1 M KCl in 20 mM Tris-HCl buffer, pH 7.6, and 0.1% Brij 35, and finally with 0.1 N NaOH. The clear fall-through eluant was collected and saved while the turbid fall-through eluant was re-applied to a second DEAE-cellulose column of similar dimension, and the clear eluant collected. The turbid eluant which followed was applied to a third DEAE-cellulose column and the column was eluted in the same manner. The pool of clear eluants amounting to about 3 liters was concentrated to 30 ml using an Amicon ultrafiltration apparatus fitted with a YM3 membrane with a 3 kDa molecular weight cut limit. One half of the concentrated solution was applied to a Sephadex G50 column (60 cm×4.3 cm) equilibrated with 20 mM Tris-HCl buffer, pH 7.6, containing 0.1% Brij 35, and the column was then eluted with the same buffer solution, and 20 ml fractions were collected.

Radiolabelling the LPXTGase. To label the LPXTGase directly for visualization on SDS gels, $^{125}$I tyramine was linked to the enzyme. Tyramine (1 μmole) was incubated for 5 hrs at 37° C. with 20 μCi $^{125}$I in the presence of iodobeads in 200 μl of 20 mM phosphate buffer, pH 6.5. 30 ul of the $^{125}$I-labeled tyramine solution was transferred to a microfuge tube, to which were added about 60 μg of concentrated LPXTGase and 50 μg of 1-ethyl-3-(dimethylaminopropyl) carbodiimide, both in 50 μl of distilled water, then 20 μl of 1 M Mes buffer, pH 4.9, and 2 μl of 10% Brij 35 were added. Finally distilled water was added to bring the volume of the incubation mixture to 200 μl and the mixture was incubated for 7 hrs at 37° C. with gentle shaking. At the end of the incubation, the volume of the incubation mixture was reduced to 50 μl by means of Speedvac, and the enzyme was precipitated with ethanol and ethylacetate as described above.

Enzyme Assay Method: Aliquots (10 μl) were removed from the column fractions and added to 1.5 ml Microfuge tubes. To each tube was added 30 μl of 40 mM Tris-HCl buffer, pH 7.6, containing 0.1% Brij 35, followed by a 10 μl suspension of bead-bound LPXTG-peptide substrate (0.5 to 0.8 μg, 100,000 to 200,000 cpm). The reaction mixture was incubated with vigorous shaking for 60 min at 37° C. After this time, 100 μl of water was added to each tube, and after vortex mixing, the mixture was centrifuged at 10,000 rpm for 5 min to pellet the beads. 100 μl of the supernatant was withdrawn and radioactivity was counted with a gamma counter.

Enzyme concentration and dry weight determination: The fractions with enzyme activity eluting from the Sephadex G50 column were combined, and the enzyme solution, amounting to about 150 ml, was concentrated to about 10 ml by YM3 ultrafiltration, after which an aliquot of 2 to 3 ml was lyophilized. The lyophilized enzyme was dissolved in 200 μl of distilled water, and the concentrated enzyme solution was divided into two preweighed Microfuge tubes. To each tube 300 ul each of ethanol and ethylacetate was added. The tubes were kept at −20° C., precipitating the enzyme, leaving most of the Brij-35 and buffer salts in the supernatant. The precipitated enzyme was pelleted by centrifugation, and the pellets what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Purification of the LPXTGase Enzyme

Bacterial strain and culture: *S. pyogenes* strain D471 was grown in 50 liters of Todd-Hewitt medium supplemented with 1% yeast extract in a fermenter. Cells were harvested when the O.D. at 650 nm reached 1.0. To harvest the cells, the culture was concentrated to about 2 liters by means of a Millipore Procon filtration apparatus, and the concentrated culture was centrifuged for 10 min at 8,000 rpm using a GSA rotor. Cell pellets, about 120 g total wet weight, were suspended in 1.5 liters of 30 mM MES buffer, pH 6.2, and the cells were pelleted again by centrifugation.

Cell lysis and preparation of crude extract: The washed cell pellets described above were suspended in 1.2 liter of 30 mM Mes buffer, pH 6.2, and cell clumps were gently dispersed with a Dounce homogenizer. To the cell suspension 10,000 units of lysin, a muralytic enzyme of a group C phage origin (60), were added and the mixture stirred for one hour at 37° C. Treatment with a low concentration of lysin resulted in localized digestion of cell wall peptidoglycan, creating holes in the cell wall. Cell membrane and cytosol exuded through these holes, releasing cytosol and part of the cell membrane as vesicles (59; 61). The cell ghosts were pelleted by centrifugation for 20 min. at 10,000 rpm with a GSA rotor, and the supernatant containing cytosol and membrane vesicles was collected. The cell ghosts were then resuspended in 600 ml of the MES buffer, the suspension was centrifuged again and the supernatant collected. The combined supernatant, termed cytosol fraction, was used as a starting material for enzyme purification. The cell ghosts, which retained the remainder of the cell membrane, were suspended in 800 ml of the MES buffer, and after adding Brij-35 to a final concentration of 0.2%, the mixture was stirred overnight at 4° C. The mixture was then centrifuged for 30 min. at 10,000 rpm and resulting supernatant, termed membrane extract, was also used as a starting material for enzyme preparation.

Preparation of LPXTG-peptide Substrate: An LPXTG-containing peptide, KRQLPSTGETANPFY (SEQ ID NO:2) from the streptococcal M6 protein, was synthesized by the Rockefeller University Peptide Synthesis Laboratory. The C-terminal tyrosine was added to allow the peptide to be labeled with $^{125}$I using iodobeads. Generally, 2 mg of the peptide was labeled with 1 mCi of $^{125}$I. The N-terminus of the labeled peptide was then linked to carboxymethyl glass beads by carbodiimide catalysis according to manufacturer's instructions. To achieve the linkage, the peptide (1.2 μmoles) was incubated for 7 hours at 37° C. with 200 mg of the glass beads (59 μmoles of carboxy termini) and 30 umoles of 1-ethyl-3-(dimethylaminopropyl) carbodiimide with gentle shaking in 2 ml of 100 mM Mes buffer, pH 4.9. The reaction mixture was placed in a small column and unreacted peptide was removed by washing the column with 300 ml of 1 M Tris-HCl buffer, pH 8.6, containing 1% SDS, then with 1 liter of distilled water. Similar bead-bound peptides in which the LPSTGE (SEQ ID NO:3) was reversed (EGTSPL) (SEQ ID NO:4) or randomly placed (TEPGSL) (SEQ ID NO:5) were synthesized, labeled and purified in the same way.

dissolved in a small volume of distilled water. This enzyme solution was used as the starting material for various chemical analyses. For dry weight determination, the precipitate was dissolved in 200 μl of distilled water and the ethanol-ethylacetate precipitation step was repeated two more times in order to remove residual detergent and salts, and the final precipitate was dried in vaccuo and the tubes were weighed.

Identification of enzyme reaction products: About 2 μg of bead-bound or free KRQLPSTGETANPFY (SEQ ID NO:2), in which the terminal tyrosine was labeled with $^{125}$I, was incubated with purified LPXTGase in 50 μl of 30 mM Tris-HCl buffer, pH 7.6, containing 0.1% Brij in separate Microfuge tubes for a varying length of time at 37° C. with vigorous shaking. For reactions with bead-bound peptide, the tubes were centrifuged at designated times in order to pellet unreacted bead-bound peptide, and 30 μl aliquots of the supernatant were spotted onto silica gel TLC plates. For reaction with free peptide, 30 μl aliquots from each tube at designated times were directly spotted on a silica gel TLC plate. The plates were developed with a solvent mixture consisting of ethylacetate-pyridine-acetic acid-water (60:30:9:24), and the reaction products were located by autoradiography. Reaction products were eluted from the plate and amino acid sequences were determined with an Applied Biosystems AB1 Procise 494 instrument by the Rockefeller University protein chemistry laboratory. Various concentrations of LPXTGase or trypsin (as control) were added to 50 μg of bovine serum albumin (United States Biochemical) under conditions described above and incubated for one hour at 37° C. A sample of the reaction mixtures was analyzed by SDS-PAGE for degradation.

The results on the purification of the LPXTGase enzyme are shown in FIGS. 1-4. Using the bead-bound $^{125}$I-labeled KRQLPSTGETANPFY (SEQ ID NO:2) peptide from S. pyogenes, which contains the LPXTG motif, an attempt was made to identify an endopeptidase in the streptococcal cell extract. In numerous initial trials, no LPXTG-cleavage activity was detected in any crude fraction or in fractions from chromatography columns. Eventually we discovered that ultrafiltration of the crude extract using a YM3 filter removed a low molecular weight substance that inhibited the cleavage activity. After removing this inhibitor by ultrafiltration, active enzyme could be prepared from both cytosol and membrane extracts. The enzyme activity in the cytosol is entirely attributable to membrane vesicles released into the cytosol rather than a soluble cytosol fraction. For example, lysin treatment of S. pyogenes results in localized digestion of the cell wall, producing holes in the cell wall. Through these holes, segments of cell membrane exude externally, which become pinched off as vesicles (Nelson et al (2001) Proc. Natl Acad. Sci U.S.A. 98: 4107-4112). When the turbid cytosol was centrifuged for one hour at 30,000 rpm, membrane vesicles along with all the enzyme activity were pelleted. A large part of the cell membrane still remained associated with the cell ghosts and more cleavage activity could be extracted from the ghost-associated membranes.

Preliminary experiments revealed that LPXTG-cleavage activity does not bind to DEAE-cellulose while most proteins did. Thus, the cytosol fraction containing membrane vesicles or the membrane extract of the cell ghost was directly applied to a DEAE-cellulose column as the first step of enzyme preparation. Free enzyme released from the membrane eluted first in the clear fall-through fraction, which was followed by the vesicle-containing turbid fraction. However, neither the clear nor turbid fall-through fractions showed an LPXTG-cleavage activity initially (FIG. 1). Thus, when the volume of the clear fall-through fraction was reduced by ultrafiltration using a 3 kDa cutoff YM3 membrane, the retentate exhibited enzyme activity. This suggests that a low molecular weight inhibitor eluted from the DEAE column together with the enzyme in the fall-through fraction, and the inhibitor passed through the membrane during ultrafiltration. As the concentration of Brij-35 in the fall-through fraction increased during concentration, it formed micelles which could not pass through YM3 membrane, and as a consequence the retentate became very viscous. Therefore, to remove Brij-35, a large volume of detergent-free Tris-HCl buffer was added to the retentate, and the ultrafiltration process was continued. During this procedure more of the enzyme inhibitor passed through the YM3 membrane along with monomeric Brij-35, increasing the activity of the enzyme in the retentate.

Figure 2:
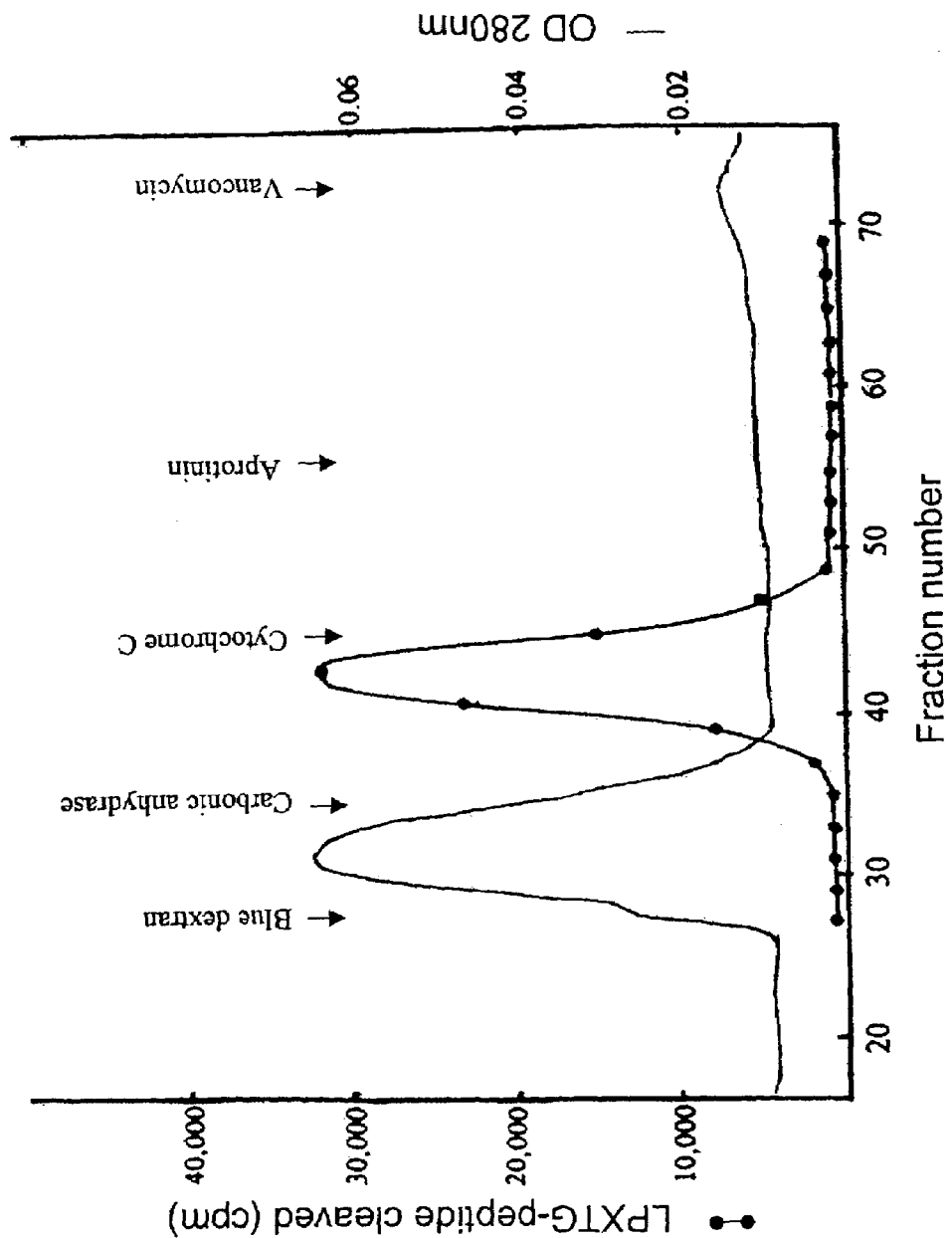
FIG. 2 shows the results of chromatography on Sephadex G50 of the clear fall-through material from the DEAE-cellulose column. The clear fall-through fractions eluting from the DEAE-cellulose column in FIG. 1 were pooled and concentrated by means of ultrafiltration. The concentrated enzyme solution was subjected to gel filtration on Sephadex G50 column and aliquots (10 µl) of fractions from the column were assayed for cleavage activity of glass bead-bound $^{125}$I-labeled LPXTG-containing peptide.

When the concentrated enzyme solution was subjected to gel filtration using Sephadex G50, an active enzyme peak eluted soon after the void volume (FIG. 2). The activity peak did not absorb UV at 280 nm, indicating that the enzyme does not contain aromatic amino acids. Comparison with the elution profiles of proteins of known molecular weights indicates that the apparent molecular weight of the cleavage enzyme to be around 14,000.

Figure 3:
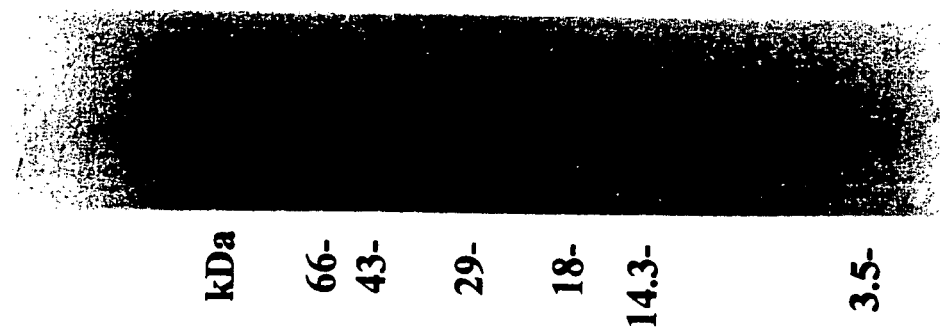
FIG. 3 shows SDS-PAGE analysis of the $^{125}$I-labeled LPXTGase. The ethanol and ethylacetate precipitated enzyme that had been labeled with $^{125}$I-tyramine was solubilized in 0.2% SDS in 100 mM Tris-HCl buffer, pH 6.8, and after boiling, the enzyme was subjected to SDS-PAGE using 16% acrylamide gel, and the dried gel was autoradiographed.
Figure 4:
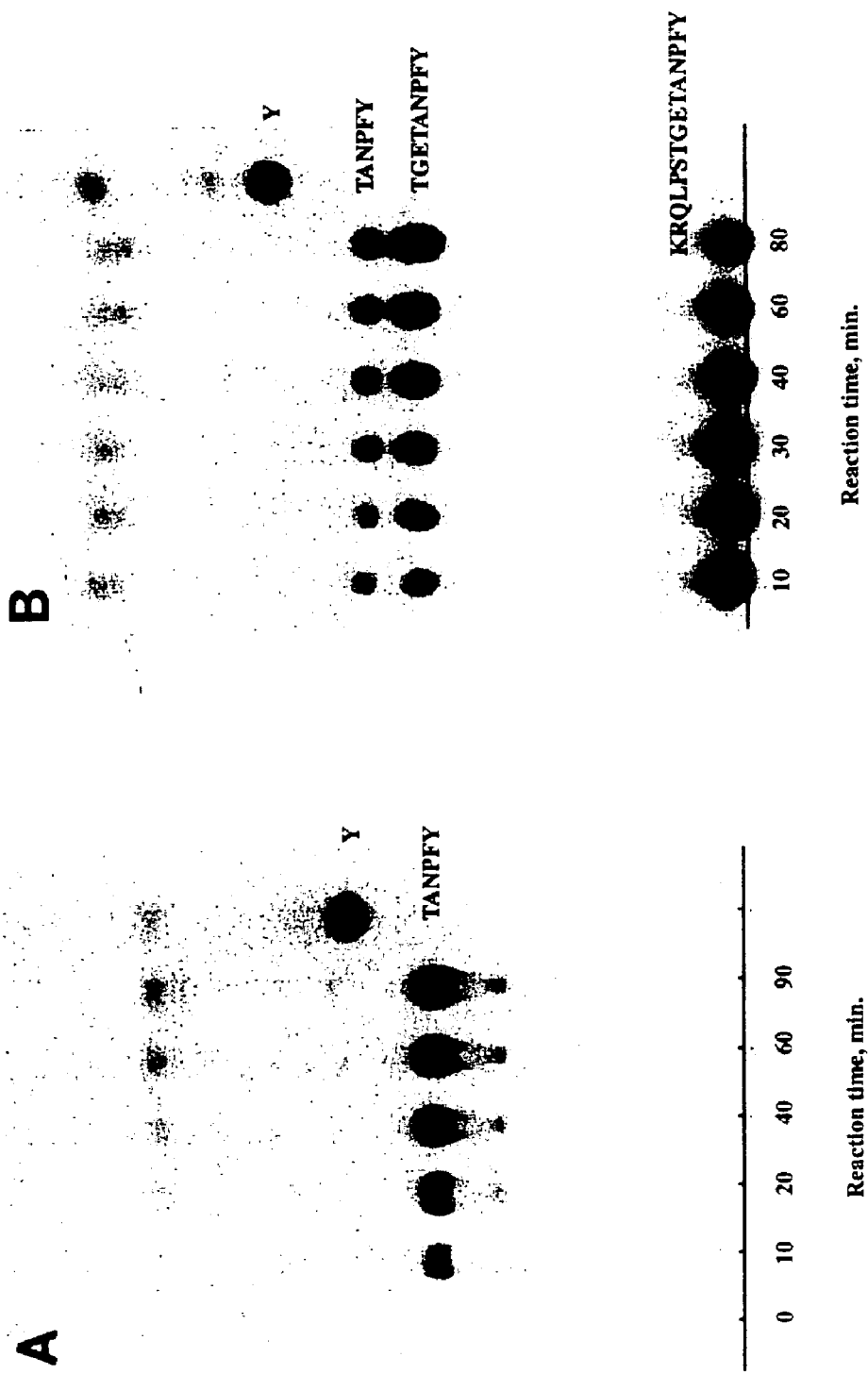
FIG. 4 shows cleavage of an LPXTG-peptide by LPXTGase. a. Bead-bound KRQLPSTGETANPFY (SEQ ID NO:2), in which the C-terminal tyrosine was labeled with $^{125}$I, was incubated with purified LPXTGase, and the reaction product was examined on silica gel TLC. b. Free KRQLPSTGETANPFY (SEQ ID NO:2), in which the C-terminal tyrosine was labeled with $^{125}$I, was incubated with purified LPXTGase, and the reaction products were examined on silica gel TLC. Y designates the location of free tyrosine. The location of other peptide sequences were identified after sequencing the peptide within their respective spots.

SDS-PAGE analysis revealed no protein bands stained with either Coomassie blue or silver, even when over 100 μg of the purified enzyme was applied to a 16% gel (not shown). However, the lack of protein bands verified the purity of the enzyme preparation. Thus, in order to detect the enzyme in polyacrylamide gels, $^{125}$I-labeled tyramine was linked to the carboxy groups of the enzyme by means of carbodiimide catalysis, and the radioactive enzyme subjected to SDS-PAGE. Radioautography of dried gels showed that most of the labeled enzyme was retained in the stacking gel and only a small amount entered the running gel (FIG. 3). When the enzyme was labeled with fluorescein isothiocyanate, and subjected to SDS-PAGE, most of fluorescent enzyme was located in the stacking gel, with a small amount entering the running gel as a series of faint bands, forming a ladder (not shown) with no fluorescent material at the 14 k Da region. These observations strongly suggest that the enzyme forms large aggregates in the presence of sodium dodecyl sulfate.

To determine where in the LPXTG (SEQ ID NO:1) motif cleavage occurred, purified LPXTGase was used to cleave a bead-bound form of the KRQLPSTGETANPFY (SEQ ID NO:2) peptide, and the cleaved fragment subjected to N-terminal sequence analysis. Results revealed that the enzyme cleaved after glutamic acid within the LPSTGE (SEQ ID NO:3) sequence releasing the TANPFY (SEQ ID NO:6) peptide fragment (FIG. 4a). On the other hand, the enzyme cleaved the free KRQLPSTGETANPFY (SEQ ID NO:2) peptide at two sites, after the serine and the glutamic acid of LPSTGE (SEQ ID NO:3), yielding TGETANPFY (SEQ ID NO:7) and TANPFY (SEQ ID NO:6) respectively (FIG. 4b). Because only these products were observed, this indicates that the trypsin (KR) and chymotrypsin (FY) substrates found at either end of the peptide were not cleaved by the LPXTGase. When the enzyme was reacted with similar bead-bound peptides or free peptides in which the LPSTGE (SEQ ID NO:3) was reversed (EGTSPL) (SEQ ID NO:4) or randomly placed (TEPGSL) (SEQ ID NO:5), no cleavage was observed (not shown). No cleavage was observed when native bovine serum albumin was reacted in a similar way. The small amount of radioactive materials observed at the solvent front originated from the impurities in the synthetic peptide. These impurities were not reactive to enzyme action. Based on its ability to specifically cleave within the LPXTG (SEQ ID NO:1) anchor motif of surface proteins, we have termed this endopeptidase "LPXTGase".

Example 2

LPXTGase Kinetics

Enzyme kinetics: Varying concentrations of $^{125}$I labeled KRQLPSTGETANPFY peptide, ranging from 20 μM to 240 μM were incubated with 2.4 μM of the purified LPXTGase in 50 μl of 50 mM Tris-HCl buffer, pH 7.6, containing 0.1% Brij 35 at 37° C. for 30 min. At the end of the reaction time, 30 μl of the reaction mixtures were spotted on silica gel TLC plates and the plates were developed with ethylacetate-pyridine-acetic acid-water (60:30:9:24). The plates were then autoradiographed, substrate and reaction products scraped off the plate and counted for radioactivity.

Figure 5:
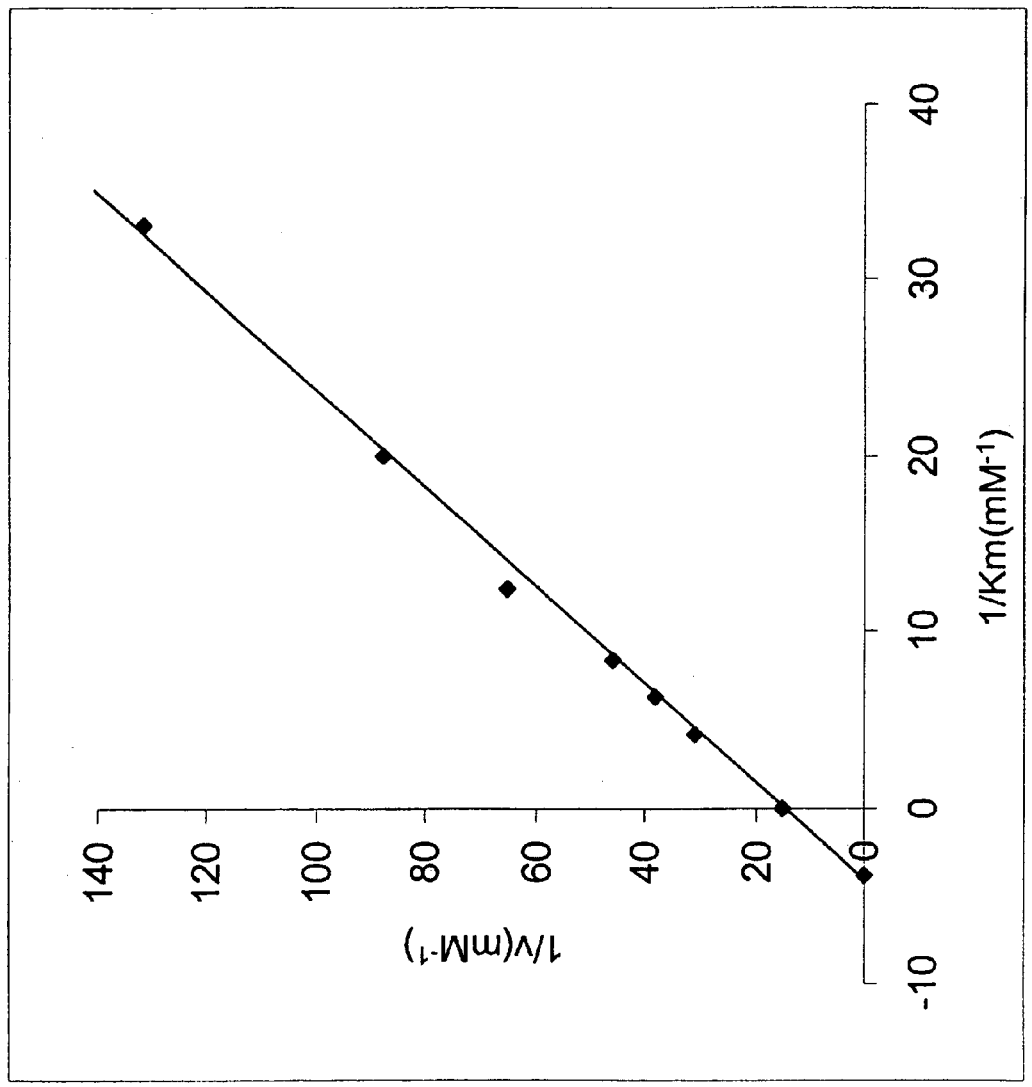
FIG. 5 shows the kinetics of cleavage of LPXTG-peptide by LPXTGase. $^{125}$I-labeled KRQLPSTGETANPFY (SEQ ID NO:2), ranging from 20 to 240 µM, was incubated for 30 minutes with 2.4 µM of LPXTGase, and the kinetics of cleavage of the peptide was determined.

As the enzyme does not contain any aromatic amino acid, neither the Lowry nor Bradford methods could be used to determine protein concentration. Thus, the enzyme concentration was determined on the basis of its estimated molecular weight (14 kDa) and dry weight. Using this, a Lineweaver-Burk plot of the kinetics of the LPXTGase was determined (FIG. 5), resulting in a Km of 0.26 mM and a Vmax of 67 μM in 30 min when 2.4 μM of enzyme was used in the assay.

Example 3

Determination of pH Optimum of LPXTGase Activity

Optimization of enzyme activity: To determine the pH optimum of enzyme activity, enzyme reactions were carried out under various pH conditions using the following buffers: Mes-NaOH (pH 5, 6, 6.5 and 7 ), Tris-HCl (pH 7.5, 8.0, 8.5 and 9 ), NH$_4$OH—HCl (pH 10), triethylamine-HCl (pH 11 and 12 ). To determine the effect of detergents on enzyme activity, enzyme reactions were carried out in the presence of 0.05% to 0.5% of Brij-35 or Triton X100. To determine the optimal duration of reaction time, the amount of radioactive peptide released from the beads were measured at 10 min. intervals up to 2 hrs.

Figure 6:
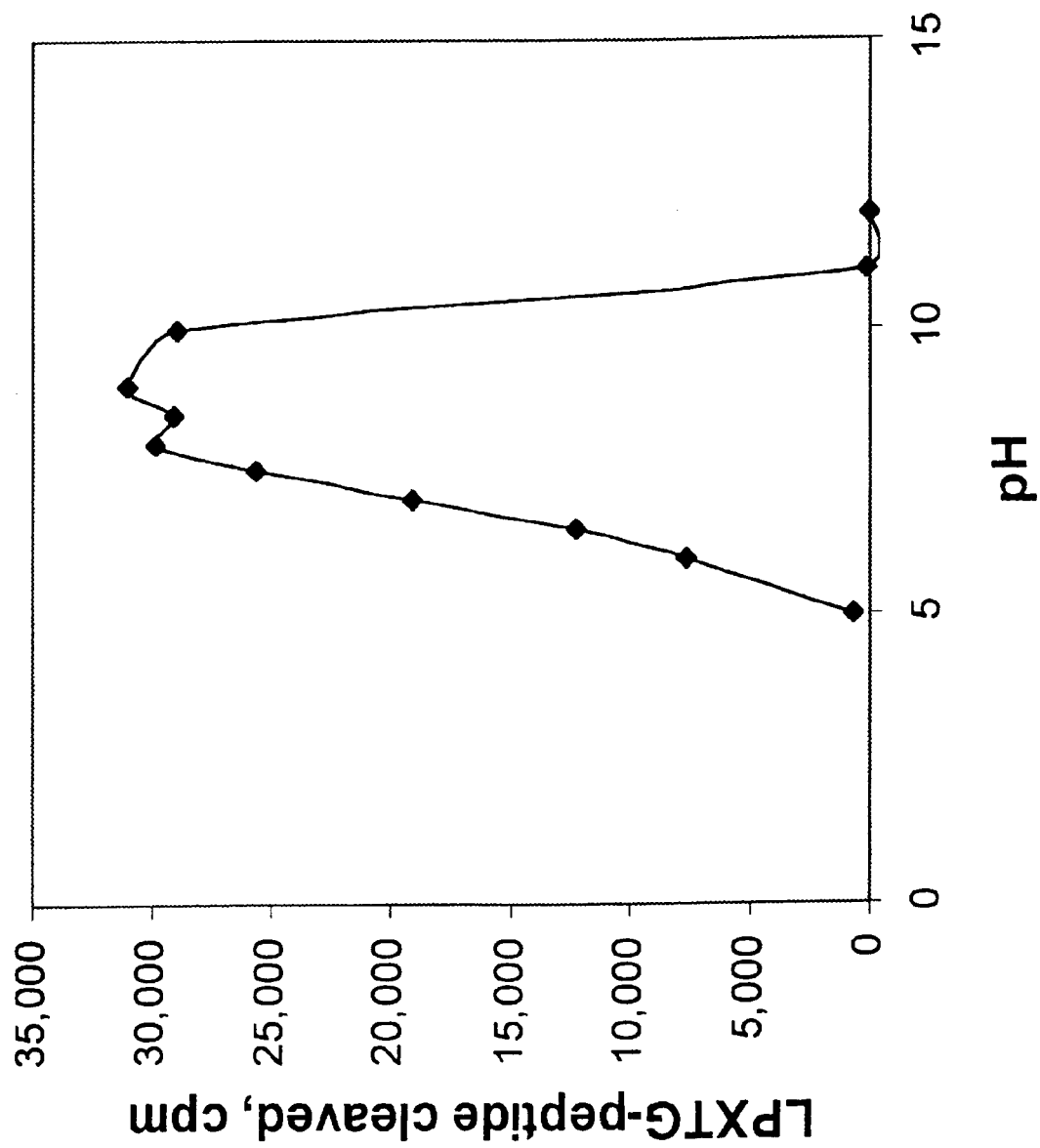
FIG. 6 shows the pH optimum of LPXTGase activity. The optimum pH for LPXTGase activity was determined, at 50 mM concentrations of various buffers. The buffers employed were: Mes-NaOH for pH 5, 5.5, 6, 6.5 and 7; Tris—HCl for pH 7.5, 8, 8.5 and 9; NH$_4$ OH—HCl for pH 10; and triethylamine —HCl for pH 11 and 12.

As shown in FIG. 6, the LPXTGase exhibited a broad pH optimum between 7.5 and 10. Below pH 5 or above 10, the enzyme activity could not be measured. In most enzyme assays, pH 7.6 was used because background activity was higher at higher pH. Enzyme activity was highest when 0.1% to 0.2% of Brij-35 or Triton X100 was incorporated. The maximal initial enzyme velocity was maintained up to the first 20 min, and after one-hour only small additional cleavage of the peptide occurred.

Example 4

Effects of Salt on LPXTGase Activity

The LPXTGase was exposed to a variety of salts and its activity tested for cleavage of the LPXTG (SEQ ID NO:1)-containing peptide. As seen in Table 1, the enzyme was found to be rather sensitive to exposure to a number of certain salts.

Example 5

Presence of Carbohydrate in LPXTGase

Carbohydrate composition of LPXTGase. The carbohydrate composition of purified LPXTGase was determined by the Rockefeller University Analytical Service Laboratory using a Waters 490 HPLC system. Successful linking of $^{125}$I-labeled tyramine to the enzyme demonstrated that it possesses free carboxy groups. Nonetheless, the enzyme did not bind to DEAE-cellulose, indicating that these carboxy groups are not surface-exposed. It seemed plausible that the charged amino acids of the enzyme are internalized and the hydrophobic amino acids are located on the exterior surface in view of the fact that the enzyme is likely to be associated with the cell membrane. However, an enzyme with a hydrophobic surface would not be very soluble in aqueous buffer, which is contrary to our findings. This suggested to us that a few residues of sugars, which would prevent surface exposure of the carboxy groups but would confer surface-hydrophilicity to the enzyme, might shield the carboxy groups allowing them to remain soluble in aqueous buffer. To test this, the enzyme was incubated with 5 mM of periodate in 20 mM phosphate buffer, pH 6, for 4 hrs at 4° C., and enzyme activity was measured. We found that this treatment nearly completely abolished the enzyme activity, whereas periodate treatment of trypsin in an identical manner showed no effect on its enzyme activity.

Figure 7:
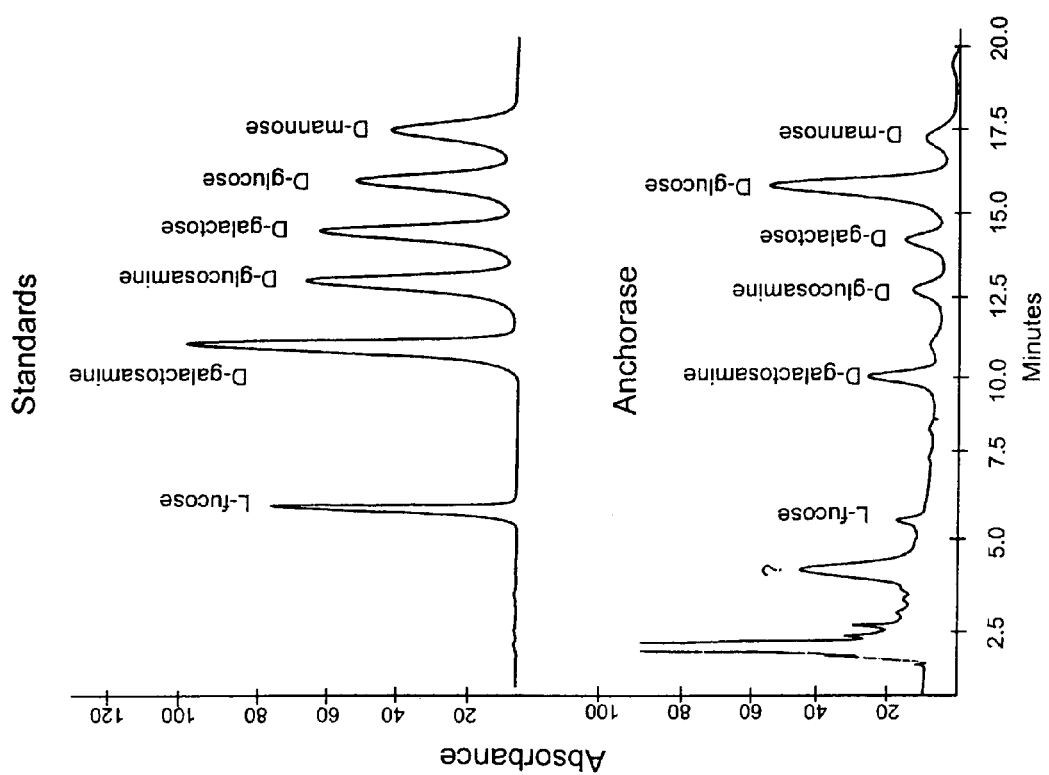
FIG. 7 shows the carbohydrate composition of LPXTGase. The carbohydrate composition of purified LPXTGase was determined by the Rockefeller University Analytical Service Laboratory using a Waters 490 HPLC system.

When the sugar composition of the LPXTGase was analyzed, L-fucose, D-galactose, D-galactosamine, D-glucose, D-glucosamine and D-mannose in a molar ratio of 1:2:3:13:2:2 (FIG. 7) were found. The aggregate mass of the oligosaccharide is 3,936 Daltons. In addition, we found an unidentified sugar that had the shortest retention time from the analytical column. The mass of this unknown sugar residue is estimated to be about 1 k Da.

Example 6

Determination of Carbohydrate Linkage Necessary for Activity of LPXTGase

Inactivation of LPXTGase activity by glycosidases: To determine the carbohydrate linkage that is necessary for activity, a fixed amount of LPXTGase was preincubated for one hour with varying amounts of glycosidases at 37° C. in a 40 μl reaction volume of 30 mM Tris-HCl, pH 7.6, containing 0.1% Brij 35 prior to testing for endopeptidase activity. At this time 10 μl of $^{125}$I-labeled, bead-bound LPXTG-peptide substrate (about 180,000 cpm) was added and the mixture was incubated at 37° C. for an additional one hour and the radioactivity of the cleaved peptide fragment was determined.

Figure 8:
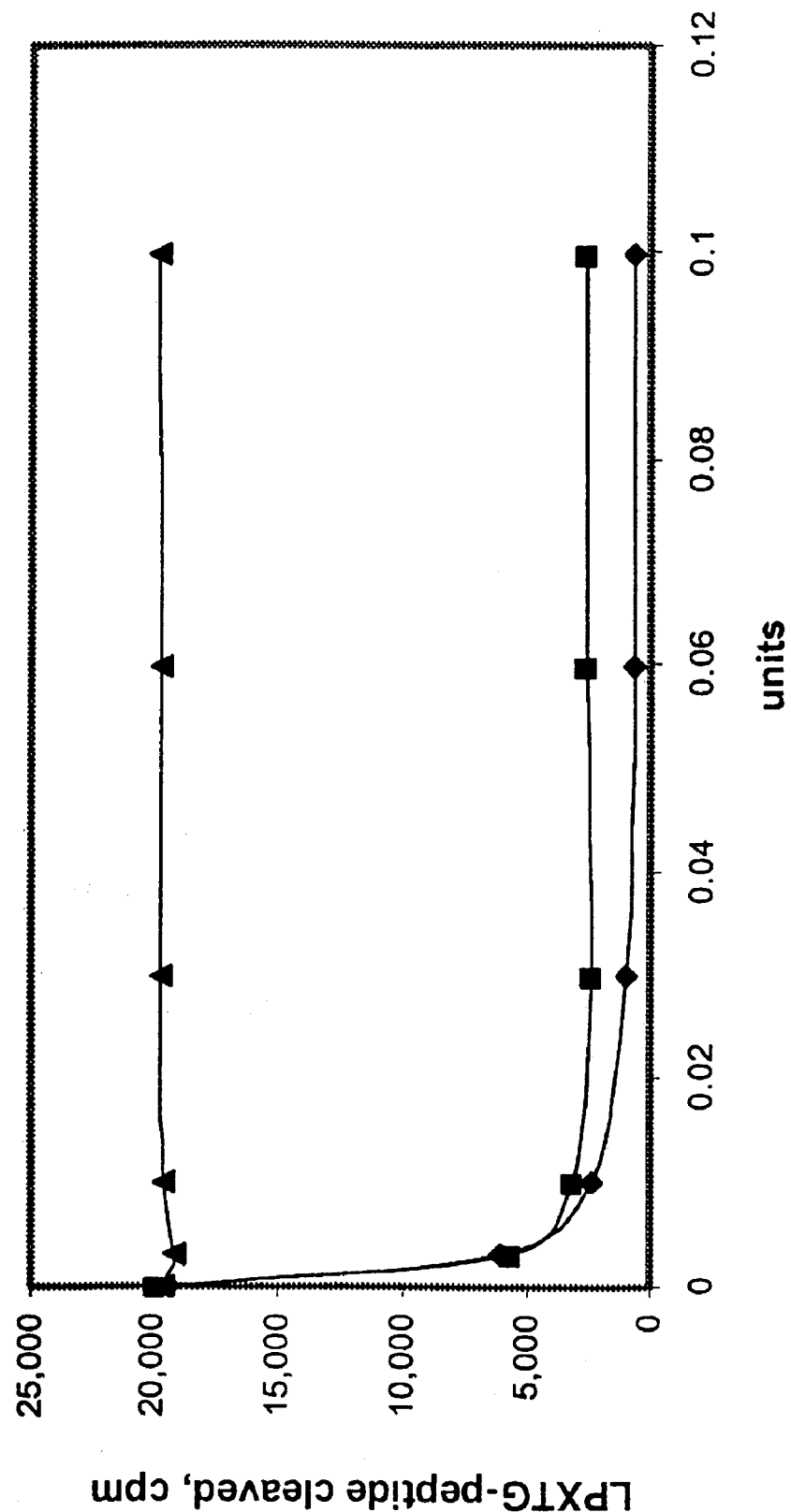
FIG. 8 shows inactivation of LPXTGase activity by glycosidases. A fixed amount of LPXTGase was preincubated for one hour with varying amounts of glycosidases at 37° C. in a 40 µl reaction volume of 30 mM Tris—HCl, pH 7.6, containing 0.1% Brij 35. At this time 10 µl of $^{125}$I-labeled, bead-bound LPXTG-peptide substrate (about 180,000 cpm) was added and the mixture was incubated at 37° C. for an additional one hour and the radioactivity of the cleaved peptide fragment was determined. Triangle: beta galactosidase. Square: N-acetylhexosaminidase. Diamond: beta glucosidase.

As shown in FIG. 8, N-acetylhexosaminidase, beta-glucosidase and beta-mannosidase abolished the LPXTGase activity, but beta-galactosidase had no effect. (Triangle: beta galactosidase. Square: N-acetylhexosaminidase. Diamond: beta glucosidase.) In addition, N-glycosidase F, which cleaves the bond between asparagine and oligosaccharides, abolished the endopeptidase activity, but O-glycosidase, which cleaves serine- or threonine-linked oligosaccharide, showed no effect (results not shown). Together, these results indicate that the carbohydrates linked to the LPXTGase are essential for catalytic activity.

Example 7

Determination of Amino Acid Composition of LPXTGase

Amino acid composition of LPXTGase: The amino acid composition of the LPXTGase was determined by the Rockefeller University Protein Chemistry Laboratory using a Waters 490 HPLC system. The concentrated enzyme in distilled water described above was used as starting material for these analyses.

Amino acid composition of the purified enzyme revealed 61 amino acid residues with an aggregate mass of 6,306 Daltons (Table 2). The enzyme contains only 11 amino acid species and contains no aromatic amino acid, which explains the failure of the enzyme to absorb UV at 280 nm and the failure to be stained by Coomassie blue. Interestingly, the enzyme contains only a few hydrophobic amino acids but an unusually large number of alanines. A most striking feature is the presence of unusual (unknown) amino acids, with an aggregate mass of about 3,000 Daltons, or about 30% of the enzyme's protein backbone. The unusual hydrophobicity of the enzyme appears to be imparted by these unknown amino acids as will be discussed below.

Example 8

Determination of the Amino Acid Sequence of a Tryptic Fragment of LPXTGase

Purification of the core protein of LPXTGase and separation of the phenylthiohydantoin-labeled tryptic fragments of the core protein: To remove covalently bound carbohydrate from the protein backbone of the LPXTGase, 1.2 mg of the enzyme was incubated for 36 hours at 37° C. with vigorous shaking with 10 units of N-glycosidase F and 10 mUs of O-glycosidase in 600 µl of 30 mM Hepes buffer, pH 7.6, containing 0.1% Brij-35 in a Microfuge tube. The incubation mixture was then banded on silica gel plates and the plates developed twice with 80% ethanol. The deglycosylated protein band was visualized by exposing the plate to iodine vapor. The protein band was eluted with 80% ethanol and concentrated to about 200 µl in a Speedvac (Savant). To the concentrated protein solution, 400 µl of 30 mM Hepes buffer, pH 7.6, containing 0.1% Brij-35, and 5 µg trypsin were added, and the mixture was incubated overnight at 37° C. To prepare phenylthiohydantoin (PTH)-labeled tryptic fragments, 3 µl of phenylisothiocyanate and 300 µl of pyridine were added to the trypsinized enzyme, after which a small volume of 1 N NaOH was added to raise the pH to 9, and the mixture shaken at 37° C. for 6 hrs. The reaction mixture was then banded on a silica gel plate and developed with a solvent mixture consisting of n-buthanol, hexane, acetic acid and water (40:40: 9:1).

UV-absorbing, PTH-labeled tryptic fragments were located, and the fragments were eluted with 95% ethanol. The slow moving fragment was then subjected to Edman degradation as follow. After hydrolysis of the PTH-peptide by a 30 min exposure to 30% trifluoroacetic acid at 50° C., the PTH-amino acid and residual peptide were separated on a silica gel TLC plate using the same running solvent. The PTH-amino acid was located under a UV light and the residual peptide was located by exposure of the plate to iodine vapor. In this manner 7 PTH-amino acids were prepared. The Rockefeller University Protein Chemistry Laboratory identified the PTH-amino acids. Of the 7 PTH-amino acids, 4 exhibited unusual masses. To help identify them, these amino acids were acid-hydrolyzed, and the Protein Chemistry Service Laboratory again analyzed the resulting products.

Despite its purity, several attempts to determine the amino acid sequence of the enzyme using an automated sequencer were unsuccessful, even when efforts were made to sequence the deglycosylated core protein. Because this suggested that the N-terminus might be blocked, we attempted to sequence an internal tryptic fragment of the core protein, also without success.

Figure 9:
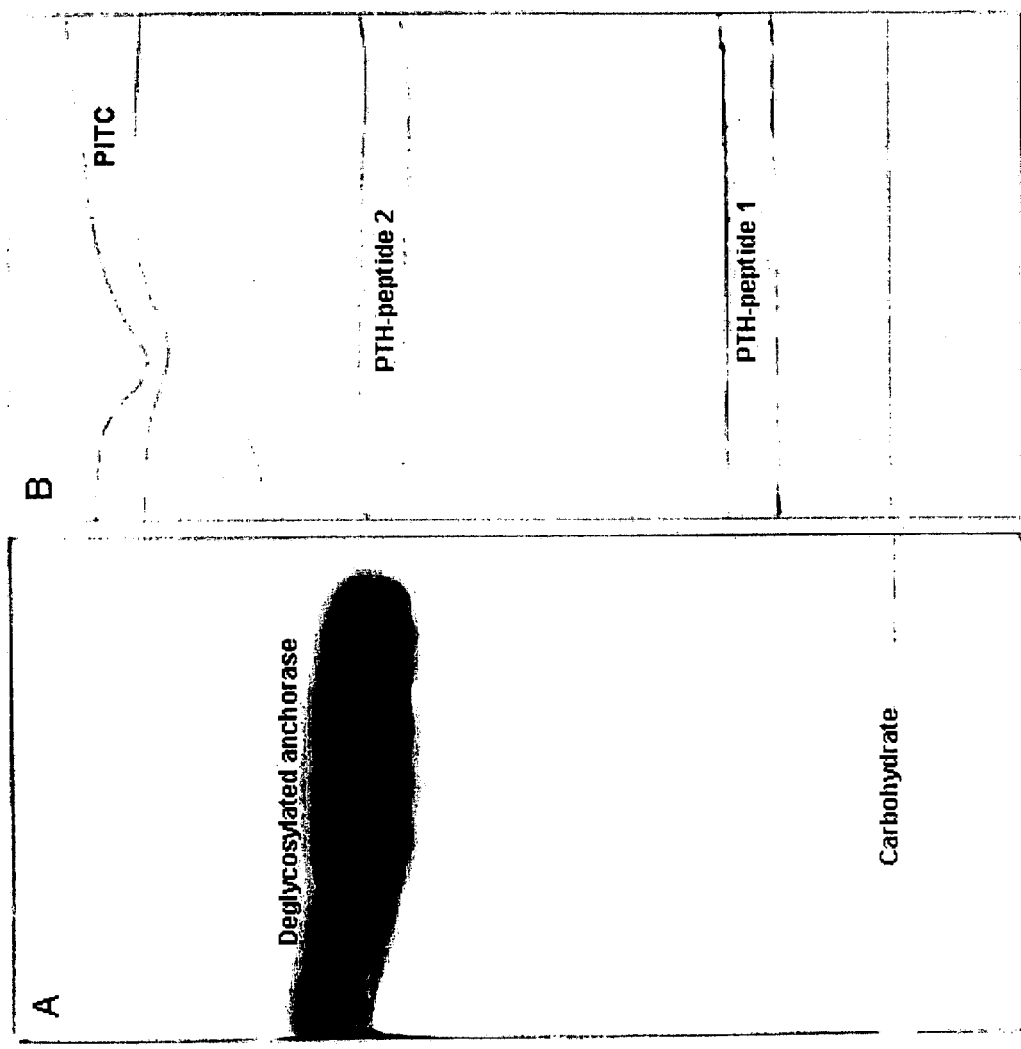
FIG. 9 shows purification of the core protein of LPXTGase and separation of the phenylthiohydantoin-labeled tryptic fragments of the core protein. a. The LPXTGase was deglycosylated and the core protein and carbohydrates were separated on silica gel TLC using 80% ethanol as a running solvent. b. The deglycosylated enzyme (core protein) was eluted from the plate and subjected to trypsin digestion and the N-termini of the tryptic fragments were linked to phenylthiohydantoin (PTH). The PTH-labeled tryptic fragments were separated on silica gel TLC using a solvent mixture consisting of n-buthanol, hexane, acetic acid and water (40:40:9:1).

The sequence failure suggested either that the standard program used for automated sequencing could not be applied to this peptide or the sequence was made up of unusual amino acids. Thus, we elected to sequence an internal fragment manually. For this purpose, the enzyme was first treated with N-glycosidase F and O-glycosidase, and the deglycosylated core protein was separated on silica gel TLC (FIG. 9a). When 80% ethanol was used as the running solvent, the core protein moved with an Rf of 0.6, which was closely followed by Hepes buffer, while the carbohydrate remained at the origin. Under identical TLC condition, untreated enzyme, bovine serum albumin, ovalbumin and trypsin remained at the origin (not shown). The high Rf value of the core protein verifies its high hydrophobicity. The core protein was then digested with trypsin and the digestion products were incubated with phenylisothiocyanate (PITC) in order to produce phenylthiohydantoin (PTH)-peptides as described in Methods. The reaction products were separated on a silica gel TLC plate using n-buthanol-hexane-acetic acid-water (40:40:9:1) as the running solvent. As shown FIG. 9b, two PTH-peptides were detected. Very faint UV-absorbing material remained at the origin, which is attributable to PTH-trypsin. Under identical TLC conditions, PTH-bovine serum albumin and PTH-trypsin also remained at the origin. The mobility of these PTH-peptides in the highly nonpolar solvent further verified the unusual hydrophobicity of the peptides. The slow moving fragment was then subjected to Edman degradation, and seven PTH-amino acids were obtained as described in Methods. Using a C-18 column, both the first and the second PTH-amino acids were identified to be PTH-proline and the seventh to be PTH-aspartic acid/asparagine. But the third, fourth, fifth and sixth PTH-amino acid exhibited retention times far longer than those of any known PTH-amino acids. The masses of these PTH-amino acids were 537.0, 537.0, 212.1 and 288.0 respectively, which do not match with the total mass of known PTH-amino acids.

Figure 10:
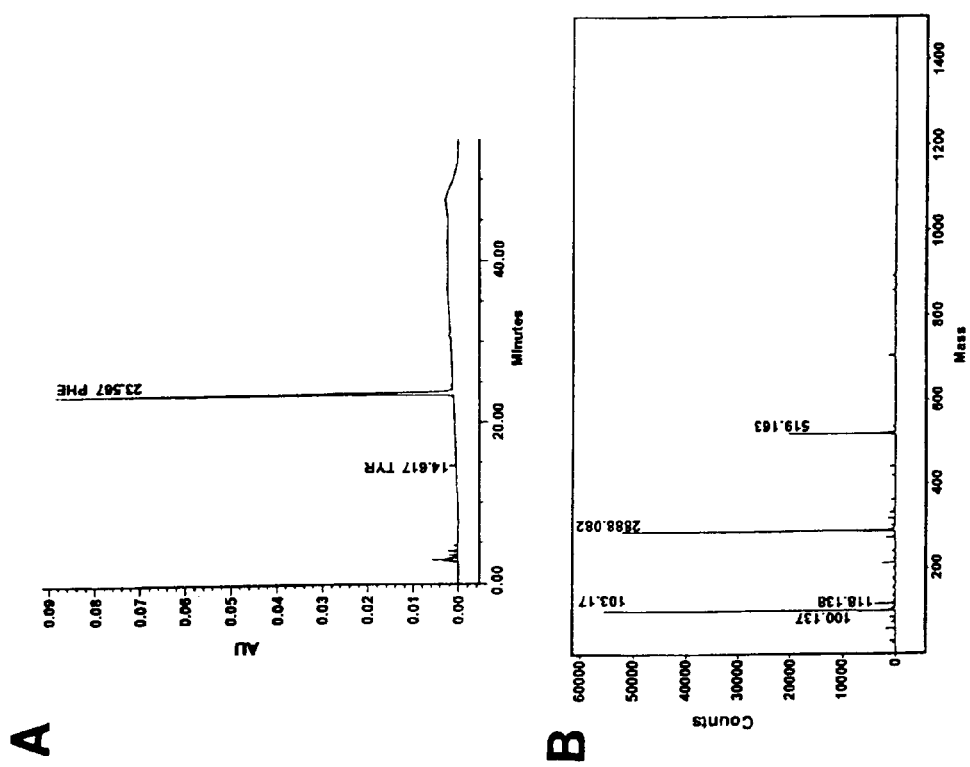
FIG. 10 shows the analysis of an unusual amino acid present in peptide fragment 1. The third PTH-amino acid of tryptic fragment 1, exhibiting a mass of 537.0 was hydrolyzed for 22 hrs. with 6 N HCl at 110° C., and the hydrolysis products were examined with reverse phase chromatography (a) and mass spectroscopy (b).

Because of their high total mass, the possibility that the third and the fourth amino acids were covalently linked to an unknown molecule was considered. Therefore, the third PTH-amino acid was acid hydrolyzed with 6N HCl for 22 hours at 110° C., and the products were analyzed by C-18 reverse phase column (FIG. 10a) and mass spectroscopy (FIG. 10b). While the reverse phase column chromatography revealed a single PTH-compound, with a retention time close to that for PTH phenylalanine, the mass spectroscopy showed three distinct peaks with masses of 102.2, 288.1 and 519.2, which do not correspond with those of known PTH-amino acids. Acid hydrolysis of the fourth PTH-amino acid gave rise to identical results as the third PTH-amino acid. Meanwhile, the acid hydrolysate of the fifth PTH-amino acid contained two species with masses of 102.1 and 212.1, the latter representing unhydrolyzed material. Acid hydrolysate of the sixth PTH-amino acid contained two species with masses of 102.1 and 288.0, the latter also representing the unhydrolzed material. Thus, we could only conclude from the species generated by acid hydrolyses that the third, fourth, fifth and the sixth PTH-amino acids are not common amino acids.

Example 9

Identification of D-alanine in LPXTGase

The presence of unusual amino acids in the LPXTGase enzyme indicated the possibility that the enzyme's core-protein might be constructed entirely or in part through the well-characterized nonribosomal peptide synthesis pathway, where amino acids are assembled into a peptide on amino acid-activating multienzyme templates. As there exists this possibility, it was considered whether some of the alanine residues might be in the D-form, a hallmark feature of non-ribosomal synthesis of peptide antibiotics (Kleinkauf, H., Dittmann, J. and Lawen, A. (1991). Cell-free biosynthesis of cyclosporin A and analogues. Biomed Biochim Acta 50(10-11): S219-224: Aker, H., Lee, S. G. and Lipmann, F. (1977). Identification of the two enzymes responsible for the synthesis of linear gramicidine. Biochemistry 16: 5727-5731.).

Studies were then conducted to determine whether some of the alanine residues might be in the D form. Of the 24 alanine residues initially identified, it was determined using the following procedures that six to seven of these alanines were in the D form rather than the L form.

Growth and $_{14}$C-alanine labeling of cells. S. pyogenes, strain D-471, was grown in 1 liter of Todd-Hewitt medium supplemented with 1% yeast extract. Cells were harvested by centrifugation at 8,000 rpm when the O.D. of the culture at 600 nm reached 0.6. The cell pellets were suspended in 1 liter of a synthetic culture medium, and after adding 100 uCi of $_{14}$C-alanine (Sigma, cat. no. A-7428) to the culture, cells were grown for one hour at 37° C. in a shaker-incubator. Cells were harvested by centrifugation and the spent medium was saved. A freshly harvested batch of late exponential cells from 1 liter culture was suspended in the spent medium containing $^{14}$C-alanine, and the cells were grown for one hour and then harvested by centrifugation. The combined cell pellets were suspended in 400 ml of 30 mM Mes buffer, pH 6.3, containing 100 mM NaCl, and cells were collected by centrifugation. The composition (in mg per liter) of the synthetic medium is as follow: Salts; $CaC_{12}$. H2O (300), $MgS_{O4}$ (200), KCl (2,000), NaCl (12,000), $NaH2P_{O4}$ (120), $N_a2HP_{O4}$ (140), FeSO 4(1). Amino acids; glutamine (2,000), tryptophan (150), all other amino acids (400). Alanine was omitted. Sugars; glucose (4,000), ribose (200), deoxyribose (200). Bases; adenine (20), guanine (20), cytosine (20), thymine (20), uracil (20). Vitamins; biotin (0.05), folic acid (1), riboflavin (1), niacin (1), pantothenic acid (1), p-aminobenzoic acid (1), lipoic acid (0.1), thiamine (1). Tryptophan and bases were dissolved in 20 ml of 0.2N HCl prior to mixing with other components. The final pH of the medium was adjusted to 7.4.

Purification of $_{14}$C-alanine labeled LPXTGase. About 3 g of the harvested cell pellets were suspended in 120 ml of 30 mM Mes buffer, pH 6.3. About 500 units of phage lysin from Group C streptococcus were added to the cell suspension and the mixture was incubated with shaking at 37° C. for 90 min. The resulting cell lysate was centrifuged at 10,000 rpm for 20 min, and the supernatant (cytosol) was saved. The pellets containing cell ghosts were suspended in 60 ml of 20 mM Tris buffer, pH 7.6, containing 0.2% Brij 35, and suspension was sonicated for 40 seconds and the sonicated suspension was stirred at 4° C. overnight. The suspension was centrifuged for 40 min. at 10,000 rpm and supernatant (membrane extract) was collected. From the combined supernatants, $_{14}$C-alanine labeled LPXTGase was purified according to the procedure described previously. Briefly, the combined supernatants were applied to a DEAE-cellulose column equilibrated with 20 mM Tris buffer, pH 6.8, and the column was eluted with 20 mM Tris buffer, pH 7.6, containing 0.1% Brij 35. Fall-through eluant was concentrated by ultrafiltration using a YM 3 membrane, and the concentrated fall-through fraction was applied to a Sephadex G50 column (49 cm×2.5 cm) equilibrated with 20 mM Tris buffer, pH 7.6, containing 0.1% Brij 35. The column was then eluted with the same buffer. The gel filtration step was repeated.

Acid hydrolysis of $_{14}$C-alanine labeled LPXTGase and purification of $_{14}$C-alanine. The $^{14}$C-labeled LPXTGase eluting from the second G50 column was concentrated to 4 ml by ultrafiltration using a YM3 membrane. The enzyme solution was lyophilized, and dried enzyme was dissolved in 0.5 ml of water. Five volumes each of ethanol and ethylacetate were added to the enzyme solution, and the mixture was kept overnight at −20° C. Flocculated enzyme aggregates were collected by centrifugation. The solvents were removed from the enzyme pellets by means of Speedvac. The dried enzyme was dissolved in 300 µl of 80% phenol, after which the enzyme solution was mixed with 3 ml of 6N HCl in capped glass vials. The enzyme was hydrolyzed by placing the vials in a 110° C. oven for 22 hours. The acid hydrolysate of the enzyme was lyophilized in order to remove HCl and phenol. The dried enzyme hydrolysate was dissolved in 1 ml of 50% ethanol, and the hydrolysate was banded on a 20×20 cm silica gel plate. The plate was developed with a solvent mixture consisting of chloroform-methanol-water (1:2:1). An autoradiogram was made from the plate, and the $^{14}$C-labeled alanine band was located. The alanine band was scraped off the plate, silica gel was placed in a small column and the column was eluted with 50% ethanol. The eluted material was dried by means of Speedvac, and the $^{14}$C-labeled alanine was dissolved in 300 µl distilled water.

Detection of D-alanine. In an initial experiment, 60 µl aliquot of $^{14}$C-labeled alanine sample (18,200 cpm) was introduced into a microfuge tube, then 4 µl of 1 M Tris buffer, pH 8.5, 0.2 unit of D-amino acid oxidase (EC 1.4.3.3, Sigma cat no. A 5222) in 2 µl and 0.2 unit catalase (EC 1.11 1.6, Sigma cat no. C 30) in 2 µl were added, and the reaction mixture was incubated for 2 hours at room temperature. Authentic L-alanine with similar radioactivity was subjected to D-amino acid oxidase and catalase in an identical manner. At the end of the reaction, 300 µl ethanol was added to the microfuge tubes and these were kept at −20° C. The resulting precipitates consisting of enzymes and excess buffer salt were pelleted by centrifugation and the supernatants containing radioactivity were concentrated to about 20 µl. The reaction products along with untreated $^{14}$C-L-alanine and $^{14}$C-pyruvic acid (Amersham, CFA 85) were loaded on a silica gel plate, and the plate was developed with chloroform-methanol-water (1:2:1). Radioactive spots were detected by exposure of the plate to an X-ray film. To the remainder of $^{14}$C-alanine sample (90,800 cpm) in a microfuge tube, 1 M Tris buffer, pH 8.5, was added to final concentration of 50 mM, after which 2 units each of D-amino acid oxidase and catalase were added to the tube. The reaction mixture was incubated for 6 hours at room temperature, and radioactive reaction products were prepared and were separated by silica gel TLC as above. Reaction products a and b shown in FIG. 3B were eluted from the plate with 70% ethanol. Products a, b and authentic $^{14}$C-pyruvic acid were loaded on a TLC plate, and the plate was developed with ethylacetate-propionic acid-water (2:1:1).

Phenylhydrazone derivatives of D-amino acid oxidase-catalae treated D-and L-alanine, and pyruvic acid. 10 µmoles each of D- and L-alanine in 100 µl distilled water were placed in microfuge tubes, after which 1 unit each of D-amino acid oxidase and catalase were added, and 1 M Tris buffer, pH 8.5 was added to a final concentration of 50 mM. The reaction was carried out at room temperature for 3 hours. Enzymes and excess buffer were then precipitated from the reaction mixtures by adding 4 volumes of ethanol. After removing the precipitates by centrifugation, the supernatant containing the reaction products were placed in microfuge tubes and were concentrated to 50 µl. 20 µmoles phenylhydrazine in 100 µl of 90% ethanol was added to the reaction products from D- and L-alanine and also to 10 µmoles pyruvic acid in 50 µl of 50% ethanol, pH adjusted to 7 with 1N NaOH, and the mixtures were placed in 110° C. oven for 15 min. Aliquots (10 µl) of the resulting phenylhydrazone derivatives were loaded on a silica gel plate and the chromatogram was developed with a solvent mixture consisting of ethylacetate-isopropanol-water-conc-ammonium hydroxide (60:30:10:1). Phenylhydrazone derivatives were detected by viewing the plate under UV.

Results $^{14}$C-labeling of cytosol and membrane extracts. In order to specifically label the alanines in the LPXTGase, streptococci were grown in the presence of $^{14}$C-alanine. Of the initial $_{14}$C-alanine in the synthetic medium totaling $1.118 \times 10^8$ cpm, the cells incorporated $1.68 \times 10^7$ cpm, or 15% of the radioactive alanine. The combined radioactive counts in the cytosol and membrane extract of these cells, which also contained free alanine, was $1.26 \times 10^7$ cpm.

Figure 11:
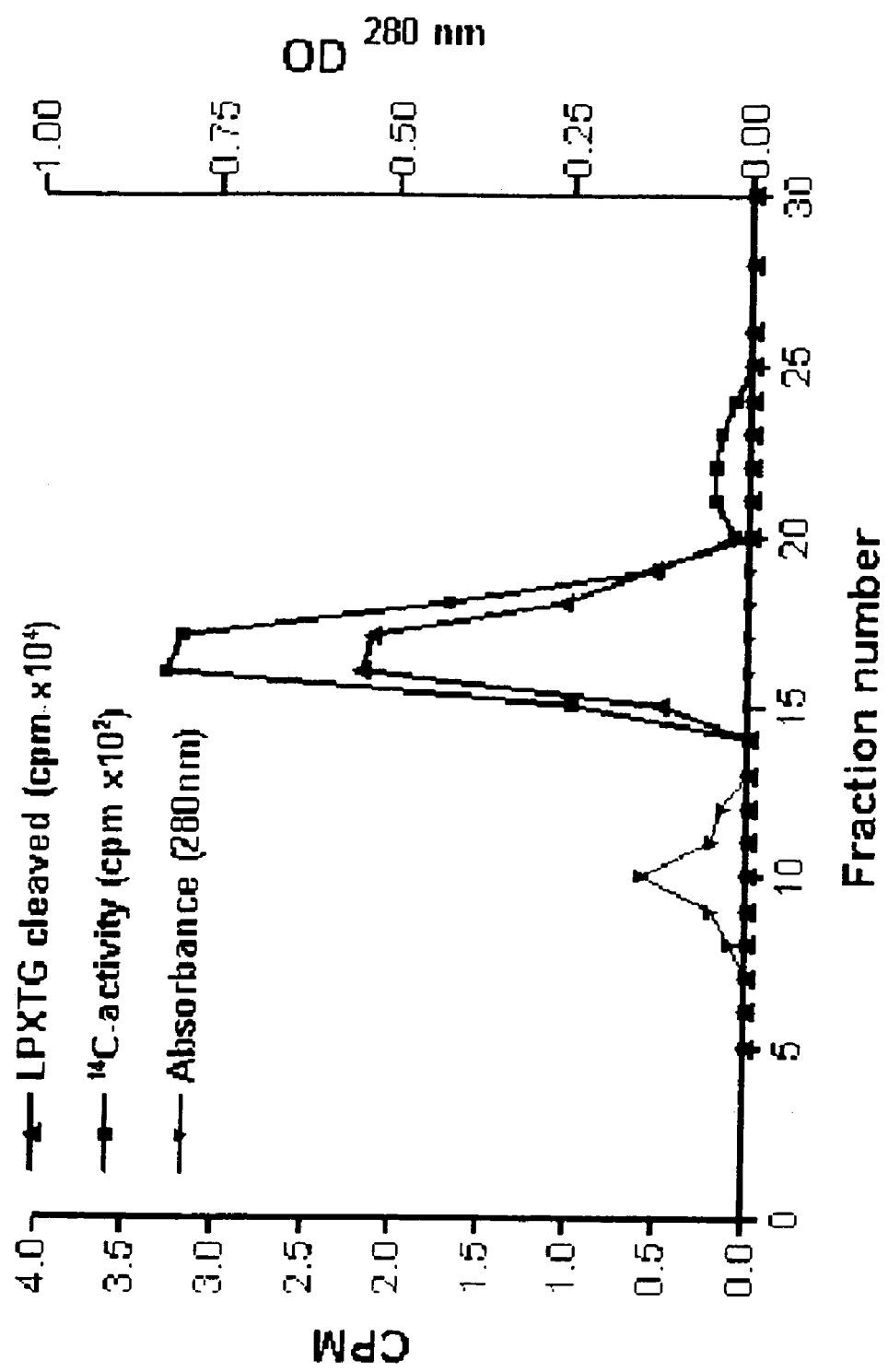
FIG. 11 shows the second Sephadex G50 chromatography of $^{14}$C-alanine-labeled LPXTGase $^{14}$C-alanine labeled cytosol and membrane extract were combined and were applied to a DEAE-cellulosed column and fall-through fraction was obtained as described in Methods. The fall-through solution was concentrated by means of ultrafiltration, and the concentrated solution was chromatographed on a Sephadex G50 (49 cm×2.5 cm) as described in Methods. LPXTGase activity was determined by measuring cleavage of bead-bound $^{125}$I-labeled LPXTG-peptide as described previously (Nelson, D., Loomis, L. and Fischetti, V. A. (2001). Prevention and elimination of upper respiratory colonization of mice by group A streptococci by using a bacteriophage lytic enzyme. Proc. Natl. Acad. Sci.(USA) 99: 4017-4112.). The peak enzyme fractions were concentrated and chromatographed again on the same G50 column. From each fraction, 50 μl aliquot was used for enzyme assay and 200 μl for $^{14}$C counts.

Purification of $^{14}$C-alanine-labeled LPXTGase. FIG. 11 shows the elution pattern of enzyme activity from the second Sephadex G50 column. The enzyme activity profile, as detected by cleavage of a bead-bound $_{125}$I-labeled LPXTG-containing-peptide (Nelson, D., Loomis, L. and Fischetti, V. A. (2001), Proc. Natl. Acad. Sci. (USA) 99: 4017-4112.), coincided precisely with the $^{14}$C activity profile. The total radioactive counts of the purified LPXTGase were $1.42 \times 10^5$ cpm. Consistent with our previous findings that the LPXTGase does not contain any aromatic amino acid, and thus does not absorb UV at 280 nm, the enzyme peak showed no UV absorption at 280 nm, verifying the purity of the enzyme.

Figure 12:
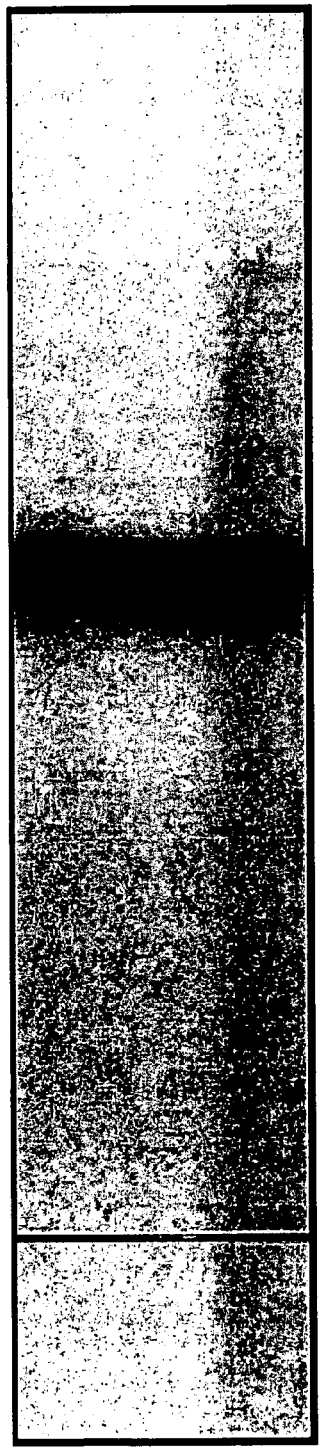
FIG. 12. Shows the purification of $^{14}$C-alanine from acid hydrolysate of purified enzyme. Acid hydrolysate of LPXTGase prepared as described in Methods was banded on most of the length of a 20×20 cm silica gel plate (A) and authentic $^{14}$C-alanine (B) was loaded separately at the right end of the plate. The plate was developed with chloroform-methanol-water (1:2:1) as running solvent and the plate was autoradiographed.
Figure 12:
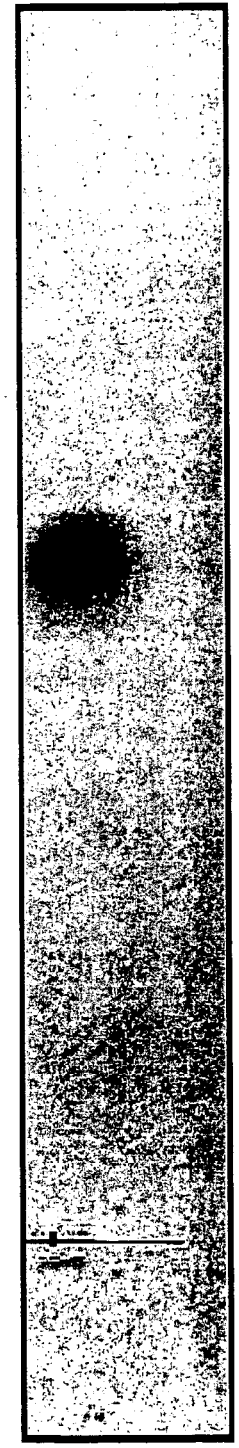

Purification of $^{14}$C-alanine from acid hydrolysate of LPXTGase. Purified LPXTGase was hydrolyzed with 6N HCl as described above, and the acid hydrolysate was subjected to silica gel thin layer chromatography using chloroform-methanol-water (1:2:1) as the running solvent. FIG. 12 shows that the $^{14}$C radioactivity was nearly exclusively present in alanine ($1.14 \times 10^5$ cpm). A very faint radioactive band was seen at Rf 0.75, which corresponded with glutamic acid. No other radioactive bands corresponding to the rest of the LPXTGase-constituent amino acids were detected. Mobilities of non-radioactive, LPXTGase-constituent amino acids on silica gel thin layer chromatography with the same solvent mixture were previously determined (results not shown).

Figure 13:
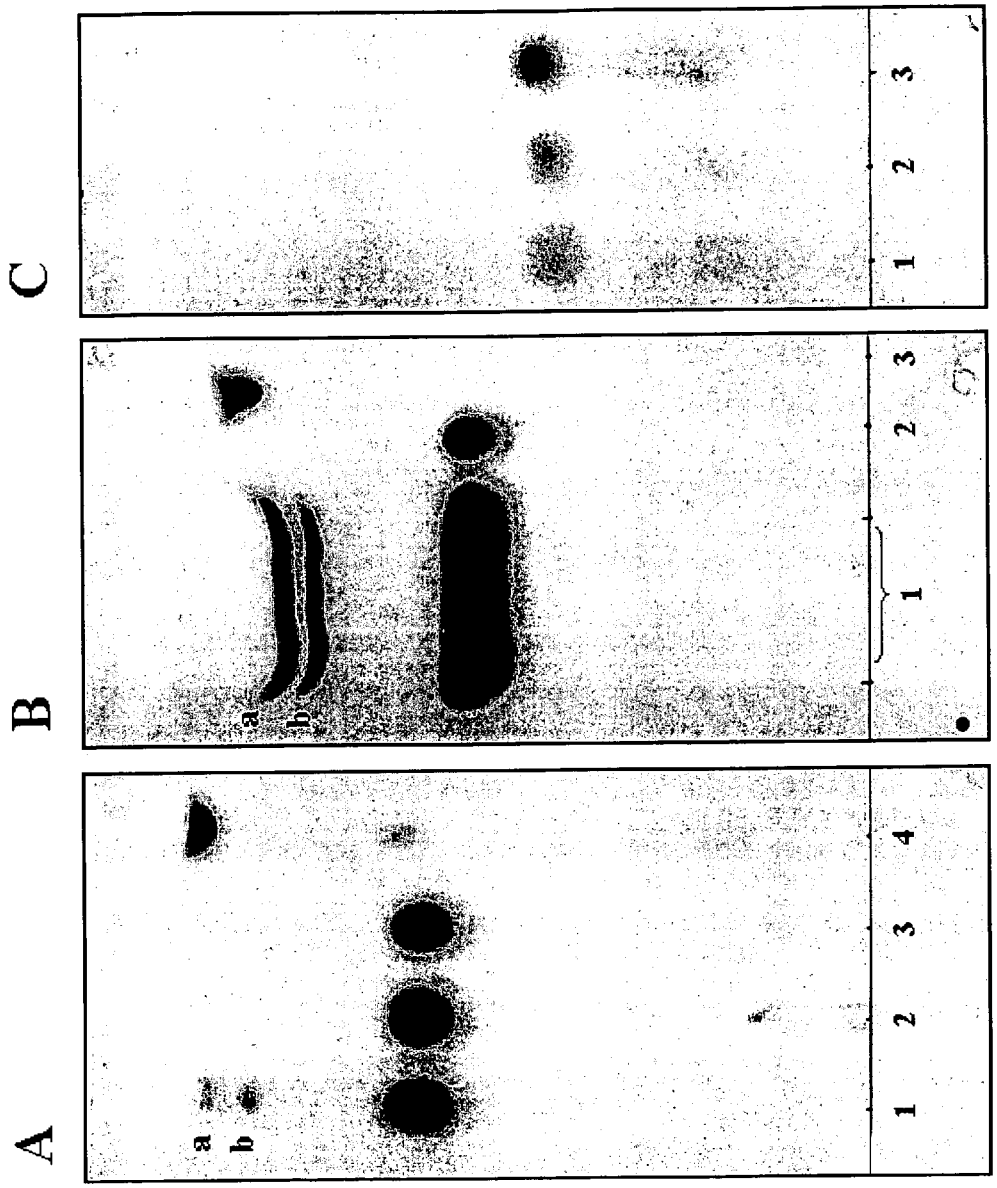
FIG. 13 shows results of chromatography of D-amino acid oxidase-catalase treated $^{14}$C-alanine from LPXTGase. A. One fifth of $^{14}$C-alanine sample from acid hydrolysate of LPXTGase in 60 μl and authentic $^{14}$C-alanine with similar radioactivity counts were subjected to D-amino acid oxidase coupled to catalase as described below. D-amino acid oxidase-catalase treated $^{14}$C-alanine sample from LPXTGase was loaded on spot 1 and similarly treated authentic $^{14}$C-L-alanine was loaded on spot 2 on the silica gel plate. Untreated authentic $^{14}$C-L-alanine and $^{14}$C-pyruvic acid were loaded on spots 3 and 4 respectively. The plate was developed with chloroform-methanol-water (1:2:1). B. The remainder of $^{14}$C-alanine sample from the acid hydrolysate was subjected to excess of D-amino acid oxidase-catalase for a longer reaction time as described below. The reaction products were banded on the left of a silica gel plate and authentic $^{14}$C-L-alanine and $^{14}$C-pyruvic acid were loaded on spots 2 and 3 respectively, and the plate was developed as in FIG. 13A. C. Rechromatography of spots a and b of FIG. 13B. Radioactive products a and b in FIG. 13B were eluted from the plate and loaded on spots 1 and 2 of a silica gel plate, and authentic $^{14}$C-pyruvic acid was loaded on spot 3. The plate was developed with ethylacetate-propionic acid-water (2:1:1) as running solvent.

Presence of D-alanine in the LPXTGase. Treatment of D-alanine with D-amino acid oxidase coupled with catalase results in the deamination of D-alanine to produce pyruvic acid, a reaction that does not occur when L-alanine is similarly treated. In FIG. 13A, D-amino acid oxidase-catalase treated $^{14}$C-alanine from the enzyme was loaded on spot 1, similarly treated authentic $^{14}$C-L-alanine on spot 2, untreated $^{14}$C-L-alanine on spot 3, and authentic $_{14}$C-pyruvic acid was loaded on spot 4 at the origins of a silica gel thin layer plate, and the plate was developed with chloroform-methanol-water (1:2:1). As shown, D-amino acid oxidase-catalase treatment of the $_{14}$C-alanine sample produced two radioactive products, a and b, of which the mobility of product a is identical with that of pyruvic acid. Product b is consistent with the mobility of the dimeric form of pyruvic acid. The yield of these products was low as reflected in the quantity loaded on the plate. To verify the presence of the dimeric form of pyruvic acid, the remaining (80% of the total) $^{14}$C-alanine from the enzyme was incubated with an excess amount of D-amino acid oxidase and catalase for a prolonged time to ensure conversion of all D-alanine to pyruvic acid, and the reaction products were chromatographed on a silica gel plate in the same manner (FIG. 13B). The same products a and b were again detected, but in higher yield. These two products were eluted from the plate, and along with authentic pyruvic acid were applied to a silica gel plate, which was developed with ethyl acetate-propionic acid-water (2:1:1) (FIG. 13C). The main radioactive spots from both products a and b showed the same mobility as authentic pyruvic acid, but minor secondary radioactive spots were also observed. The fact that products a and b from FIG. 13B gave rise to nearly identical radioactive spots on subsequent chromatography using a different solvent (FIG. 13C), indicates that these two products are inter-convertible. The total radioactive counts in products a and b in FIG. 13B were 15,200 cpm, and 9,400 cpm respectively, which combined represents 27% of the total radioactivity in the $^{14}$C-alanine sample. As there are 24 alanine residues in the LPXTGase, 6 to 7 alanine residues are in the D-isoform. These numbers are based on the assumption that all D-alanines present in the alanine sample were converted to pyruvic acid after D-amino acid oxidase and catalase treatment.

Figure 14:
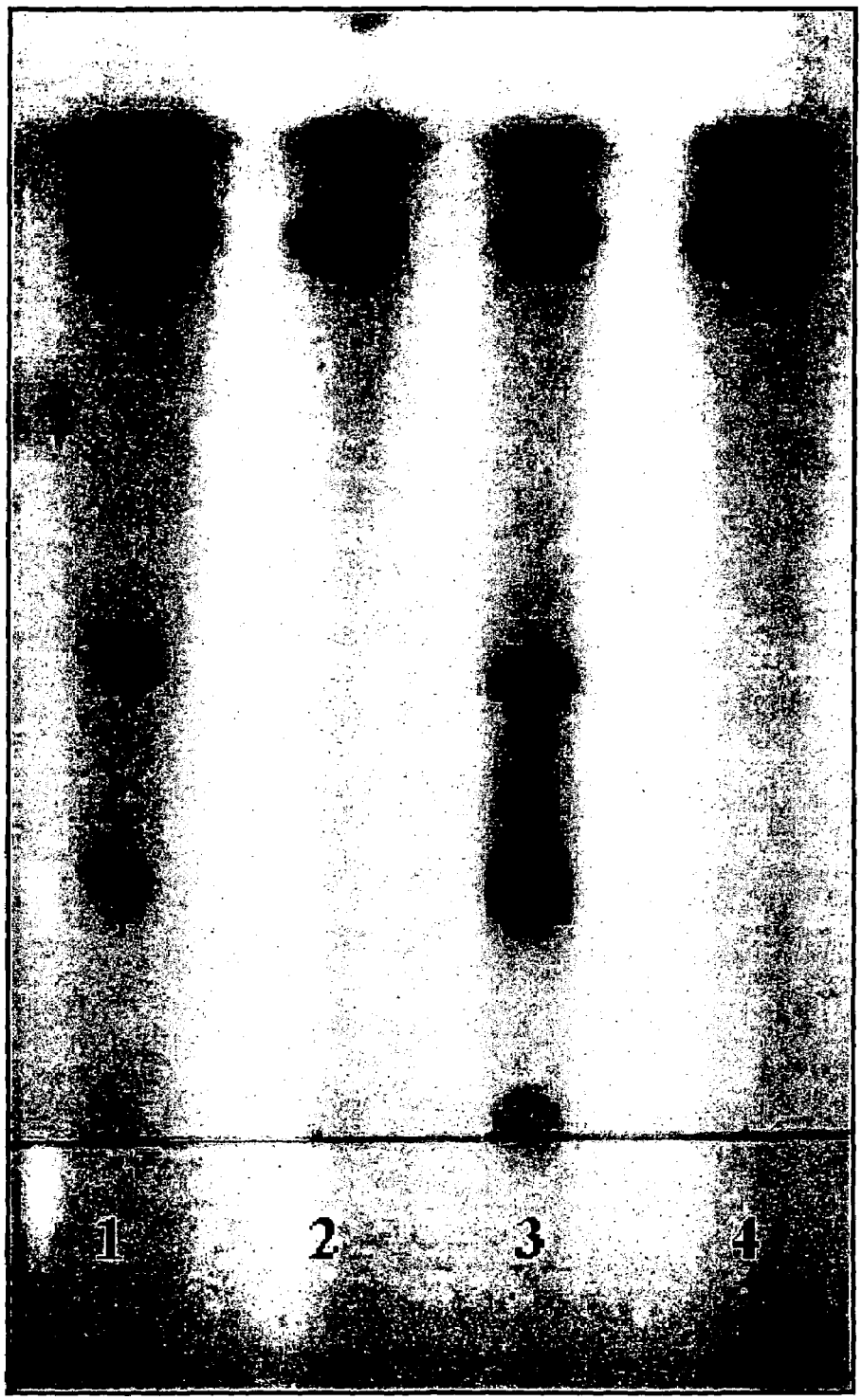
FIG. 14 shows phenylhydrazone derivatives of the products from D-amino acid oxidase-catalase treated D-alanine, L-alanine, and phneylhydrazone derivatives of pyruvic acid. Phenylhydrazone derivatives were prepared as described below. Tracks 1 Phenylhydrazone derivatives of the products from D-amino acid oxidase-catlase treatment of D-alanine. Track 2; phenylhydrazone derivatives of the products from D-amino acid oxidase-catalase treatment of L-alanine. Track 3; phenylhydrazone derivatives of pyruvic acid. Track 4; phenylhydrazine. Running solvent was ethylacetate-isopropanol-water-conc ammonium hydroxide (60:30:10:1).

Phenylhydrazone derivatives of D-amino acid oxidase-catalase treatment of D- and L-alanine, and pyruvic acid. In order to verify that pyruvic acid is present in both monomeric and dimeric forms resulting in derivatives a and b, the following procedure was followed and results were obtained. Track 1 of FIG. 14 shows phenylhydrazone derivatives of the reaction products arising from D-alanine after treatment with D-amino acid oxidase and catalase. Derivatives a and b are clearly present in this track. No phenylhydrazone derivative is seen when L-alanine treated with D-amino acid oxidase-catalase was reacted with phenylhydrazine (track 2). Track 3 shows phenylhydrazone derivatives arising from authentic pyruvic acid, which are identical to the migration pattern of derivatives a and b in track 1. Taken together, these results indicate that pyruvic acid exists both as monomer and dimer forms.

Thus, in summary, we have identified the presence of at least 6 D-alanine residues in the LPXTGase enzyme.

Example 10

Identification and Purification of an Inhibitor of LPXTGase

Figure 16:
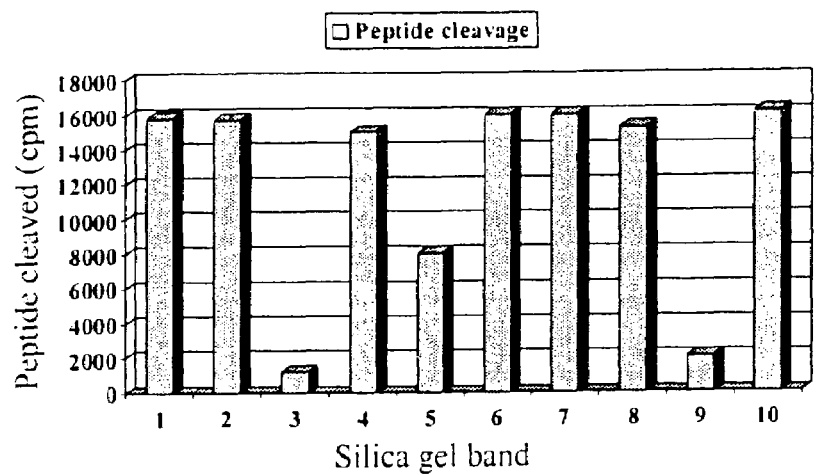
FIG. 16 shows the inhibition of LPXTGase activity on its substrate using the bands eluted from the silica gel column. Bands 3 and 9 showed the greatest inhibitory activity.

An inhibitor of the LPXTGase was purified from the membrane extracts that were used for purification of the LPXTGase. Below are the steps used to isolate and purify the inhibitor of LPXTGase. As shown below, after chromatography through a DEAE cellulose column, the fall through material contained active inhibitory material with most of the contaminating molecules adherent to the column. Further purification of the inhibitor was achieved through a silica gel column. Bands in the silica gel were eluted and tested for their ability to prevent the activity of the LPXTGase on its substrate. As shown in FIG. 16, bands 3 and 9 showed the most inhibitory effects.

Cell growth and Harvest: S. pyogenes, group A strain, was grown in 50 liter of Todd-Hewitt culture medium supplemented with 1% yeast extract in a fermenter. The cells were harvested when OD at 650 nm reached around 1.0. Cell harvest was achieved by concentrating the culture to about 2 liter by means of a Millipore filtration apparatus, then centrifuging the concentrate at 8,000 rpm for 10 minutes each with a Sorval GSA rotor. The cell pellets were suspended in 600 ml of 30 mM Mes buffer, pH 6.5, and the cells were pelleted again by centrifugation. About 100 g cell pellets by wet weight were obtained.

Cell lysis and preparation of cell wall digest and cytosol fractions: The cell pellets above were suspended in 1.2 liter of 30 mM Mes buffer, pH 6.5, and, in order to disperse cell clumps, 50 ml aliquots of the suspension were subjected to 20 strokes each in a Dounce homogenizer. To the homogenized cell suspension, 10,000 units of lysin, a muralytic enzyme, were added and the mixture was stirred for two hours at 37° C.

Lysin treatment causes localized digestion of cell wall and causes cell membrane to exude out and rupture of the membrane ensues, resulting in release of cytosol. At the end of lysin treatment, the suspension was centrifuged at 8,000 rpm using a GSA rotor for 30 minutes, and the resulting supernatant was collected. The pellets were resuspended in 600 ml of the same Mes buffer, and the suspension was centrifuged in the same manner. The combined supernatant, containing cell wall digest and cytosol, was used as the starting material for the inhibitor preparation.

DEAE-cellulose chromatography of the cell wall digest and cytosol fractions: To about 1.8 liter of supernatant above, Brij 35 was added to final concentration of 0.1%, and the supernatant was applied to a DEAE-cellulose column (16 cm×4.3 cm) equilibrated with Tris-HCl buffer, pH 6.8, and the elution was monitored by UV absorption at 280 nm. About a half liter of clear UV absorbing solution eluted first, which was then followed by turbid UV absorbing solution. After all of the applied supernatant entered the column, the column was washed with 20 mM Tris-HCl buffer, pH 7.6, until no more UV absorbing solution eluted. Generally 400 ml of the washing buffer was required. Both clear eluants were collected, and the turbid eluant was applied again to a second DEAE-cellulose column of similar dimension, and clear eluant collected. The turbid eluant which followed was applied to a third DEAE-cellulose column and the column was eluted in the same manner. The pool of clear eluants amounting to about 3 liters was used as the source of the inhibitor for further purification. Step elution with 0.1M KCl and 0.2N NaOH released no active material.

Inhibitor activities in the eluants were determined my measuring inhibition of the LPXTGase in the presence of eluant fractions. LPXTGase activity, in turn, was determined by measuring the cleavage of a synthetic peptide containing LPSTGE (SEQ ID NO:3) sequence. Construction of the peptide substrate and experimental procedure for determination of the enzyme activity are as follow. The tyrosine residue of a synthetic peptide, KRQLPSTGETANPFY (SEQ ID NO:2), was labeled with I-125, then the amino terminus of the peptide was covalently linked to glass beads through the carboy group lodged on the bead surface (Sigma, carboxymethyl glass, G-3910). The linkage was catalyzed by a carbodiimide, 1-ethyl-3-(3-dimethylaminopropyl)carbodiimide. The bead-bound, radioactive peptide was incubated at 37° C. in a microfuge tube with LPXTGase with vigorous shaking, and after one hour of reaction the reaction mixture was centrifuged. The cleaved radioactive peptide fragment, TANPFY, remained in the supernatant whereas uncleaved, bead-bound radioactive peptide pelleted. The radioactivity in the supernatant was measured to determine the LPXTGase activity.

Ultrafiltration and lyophylization: The clear flow through eluant from DEAE-cellulose columns amounting to 3 liters in volume was subjected to ultrafiltration using a 400 ml capacity Amicon Ultrafiltration apparatus and aYM3 membrane (mol. wt. cutoff 3,000). Activity inhibiting the LPXTGase passed through the membrane together with other low molecular weight substances, while proteins and bulk of Brij 35, as micelles, were retained in the ultrafiltration chamber. The filtrate fluid was lyophilized and 4 to 5 g dry residue was obtained.

Silica gel column chromatography: The lyophilized dry residue was dissolved in 30 to 40 ml of distilled water, which gave a nearly saturated solution. Insoluble residue was removed by centrifugation and the clear supernatant was collected. To this solution about 50 g of 70-140 um diameter silica gel granules (Sigma Silca gel, S-4133) were added and the thick slurry was placed on a heating plate with 60° C. set temperature in a hood. Water was evaporated to dryness, which effected adsorption of the substances in the solution to the gel granules. In order to remove hydration water from the gel granules, 100 ml of absolute ethanol was added to the dried silica gel, and the solvent was evaporated in the same manner. The dried silica gel granules with adsorbed materials were slowly introduced into a column (23 cm×2.3 cm) which was half filled with ethylacetate. The slurry in the column was stirred with the handle side of a spatula to drive off air bubbles, and silica gel granules allowed to settle. Excess ethylacetate was eluted off and the column was further eluted with 400 ml of ethylacetate. The fraction that inhibits the LPXTGase activity was then eluted from the column with a solvent mixture consisting of 50% ethylacetate, 30% methanol and 20% water. During this elution, the elution of a substance with a brownish orange color was followed as the enzyme inhibitor comigrated with this colored substance. The elution solvent of this eluant was evaporated on a heating plate with 60° C. set temperature placed in a hood, and about 2 g of dry residue was obtained. The dried residue was sparingly soluble in the elution solvent but was very soluble in water or in 50% methanol.

Figure 15:
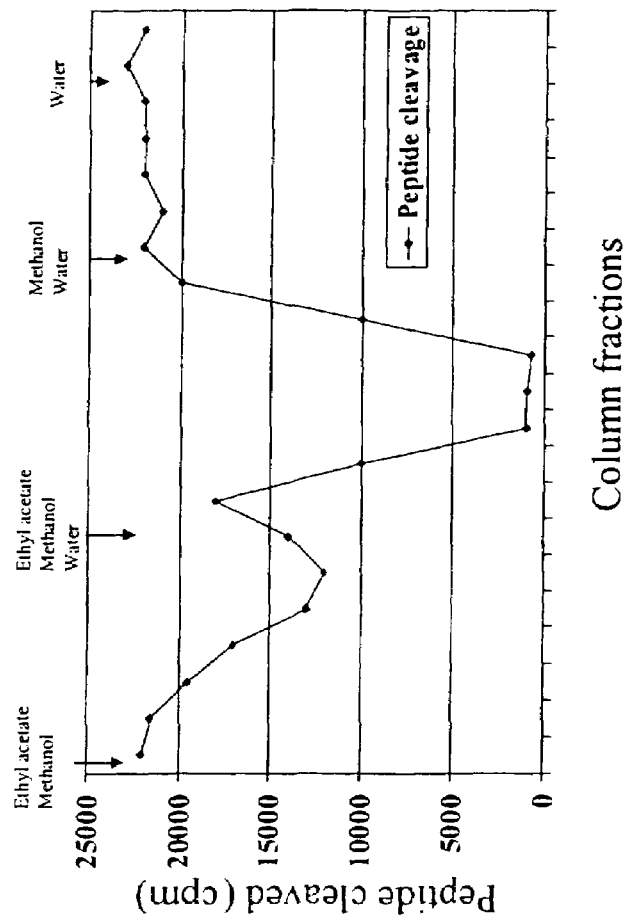
FIG. 15 shows the elution of the LPXTGase inhibitor isolated from Streptococcal membrane extracts using the flow-through from a DEAE column, followed by ultrafiltration through a YM3 membrane, with final purification through a silica gel column.

Silica gel thin layer chromatography (FIGS. 15 and 16): The dried inhibitor fraction above was dissolved in 15-20 ml of 50% methanol, and the solution was loaded onto silica gel plates (20×20 cm, Silica Gel60 F254, EM Science). Each plate was loaded with up to 200 mg of the inhibitor fraction as a broad band of up to 4 cm wide, and the plates were developed in a solvent mixture consisting of 60% ethylacetate, 30% pyridine and 10% water. When solvent front reached the top of the plates, the plates were dried and they were redeveloped in the same solvent. The redevelopment process was repeated up to 30 times. During each development the main band containing the matrix M, which was opaque when viewed through light, moved 1 to 2 mm, but in each development some compounds that were associated with the Matrix M became slowly released and these compounds moved somewhat faster. After 30 consecutive developments, the main opaque band containing the Matrix moved 4 to 5 cm, and two additional opaque bands (bands 5 and 9) appeared; one of which moved half way to two thirds of the length of the plates and the other moved to the top of the plates. These three opaque bands exhibited inhibitory activity toward the LPX-TGase. On the other hand only the top band showed both inhibitory activity toward cell growth and LPXTGase. The top band generally contained 7 to 10% of the mass loaded onto the plates. Material in this band is sparingly soluble in water or in 50% methanol, but is very soluble in chloroform-methanol mixture.

The top dual active opaque band was eluted from the plates with chloroform-methanol mixture (7:3), banded on silica gel plates and the plates were developed in a solvent mixture consisting of 50% xylene, 30% pyridine and 20% methanol. The plates were run 5 times. The inhibitor activity moved three quarters of the length of the plates. This active band consisted of myriad of pinhead opaque islets. UV absorbing impurities and one red colored band moved to the top or near the top of the plates, while a band of inert opaque material remained near the origin. Mass spectroscopic analysis of the active band indicates that it contains a series of related molecules which differ from one another by 44 Dalton mass.

Inhibition of cell growth was determined by the following manner: Aliquots of 2 to 10 μl of the eluates from respective bands of silica gel plates were introduced into small test tubes (74×8 mm) and solvent was dried off in a 110° C. oven, after which 600 μl of Todd-Hewitt medium was added to the tubes. To each tube 2 μl of overnight culture of test bacteria was introduced and bacterial growth was observed.

Figure 17:
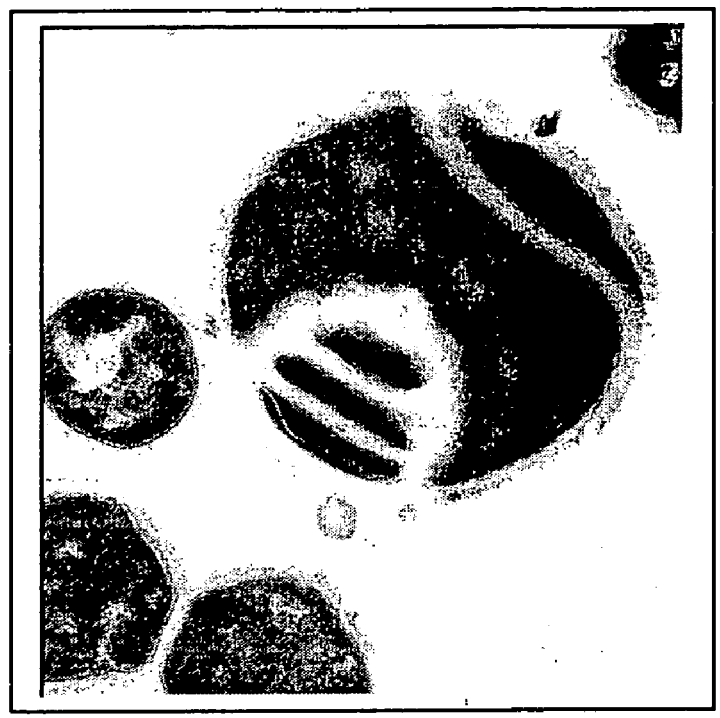
FIG. 17 shows the morphological effect of subinhibitory concentrations of the purified LPXTGase inhibitor on the cell walls of Streptococcus. Significant morphological changes are observed in organisms grown in the LPXTGase inhibitor, including thickening of the cell walls.

When the purified inhibitor was tested for its effects on the growth of streptococci, it was found to completely inhibit the growth of the organisms. In the presence of sub-inhibitory concentrations of the inhibitor, the organisms are able to grow, but morphological analysis by electron microscopy revealed that the organisms have thickened cell walls and their diameter is double that of normal cells (FIG. 17). When the inhibitor was tested against Methicillin resistant *S. aureus*, similar results were observed. Other organisms tested for their sensitivity to the inhibitor were *E. coli, B. pumulis, S. epidermidis, S. gordonii, S. mutans*, and *S. sanguis*, all of which were sensitive. *Pseudomonas aeruginosa* was the only organism tested that was resistant to the inhibitor at the concentrations used.

Figure 18:
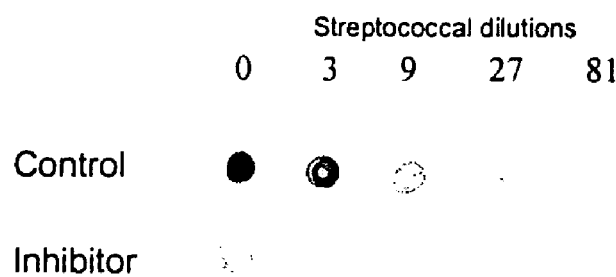
FIG. 18 shows the effect of sub-inhibitory concentrations of the LPXTGase inhibitor on the presence of surface M protein (a molecule that is anchored via the LPXTG motif) in Streptococcus. Significantly less M protein is expressed in bacteria grown in the presence of the LPXTGase inhibitor.

When streptococci were grown in the presence of the inhibitor at sub-inhibitory concentrations, and the equivalent number of cells were tested for the presence of surface M protein (a molecule that is anchored via the LPXTG (SEQ ID NO: 1) motif), it was found that inhibitor-grown streptococci expressed significantly less M protein than control bacteria (FIG. 18).

Figure 19:
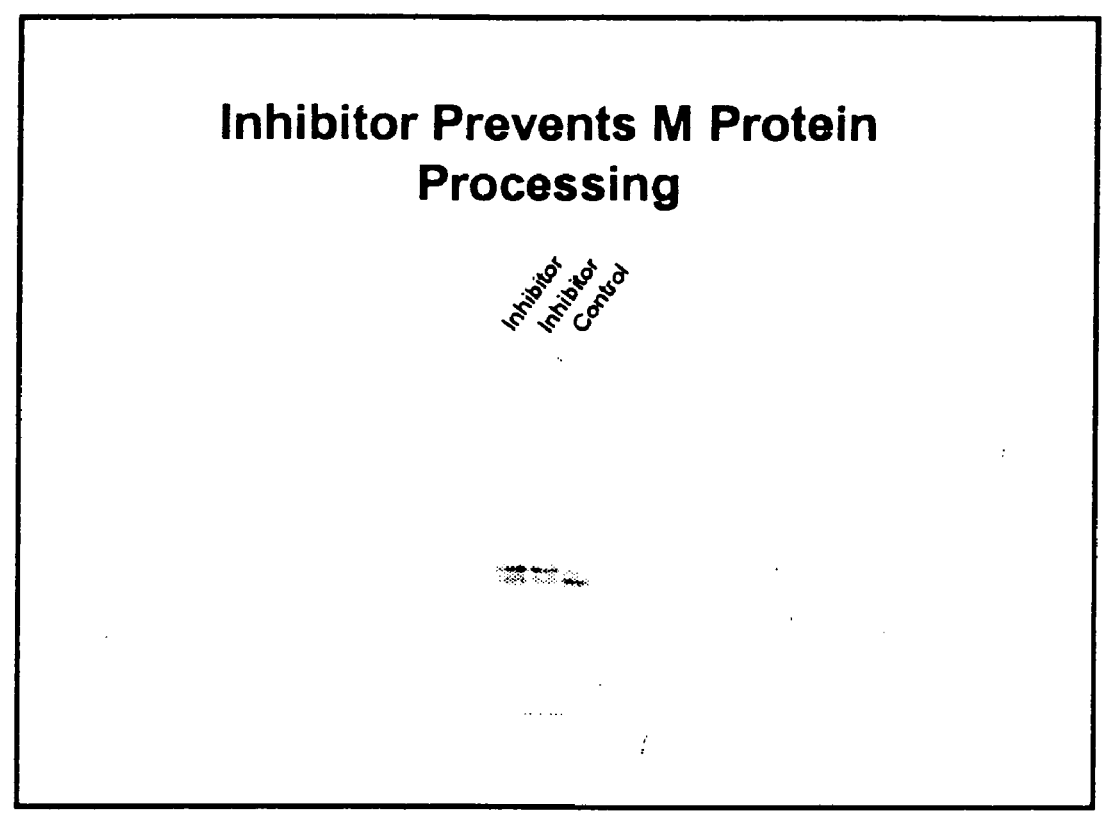

Furthermore, when the M protein was examined from inhibitor-treated and normal organisms, it was found that the inhibitor-grown organisms had a larger M protein suggesting that the LPXTGase was blocked from cleaving the C-terminal region of the molecule (FIG. 19).

Additional experiments revealed that streptococci grown in the presence of the inhibitor were phagocytized and killed by phagocytes in a phagocytosis assay whereas this was not the case with normal streptococci grown in the absence of the inhibitor.

TABLE 1

Effect of salts on LPXTGase activity

| Salts | mM | peptide cleaved, cpm | % of control |
|---|---|---|---|
| Sodium chloride | 100 | 6,720 | 16 |
| Potassium chloride | 100 | 8,608 | 20 |
| Hydroxylamine-HCl | 100 | 11,200 | 27 |
| Magnesium chloride | 20 | 8,615 | 20 |
| Calcium chloride | 20 | 9,706 | 23 |
| Putrescene chloride | 20 | 8,710 | 21 |
| Sodium phosphate | 20 | 20,646 | 49 |
| Sodium sulfate | 20 | 23,454 | 57 |
| EDTA | 20 | 2,147 | 5.2 |
| Control (no salt) | | 41,530 | 100 |

Reaction mixtures contained, in 50 ul of 40 mM Tris-HCl, pH 7.6, and 0.1% Brij 35, a fixed amount of LPXTGase, $^{125}$I-labeled LPXTG-peptide (about 180,000 cpm), and indicated concentrations of various salts. The reaction mixtures were incubated for one hour at 37° C., and the peptide cleavage was determined as described in Methods.

TABLE 2

Amino acid composition of LPXTGase

| Amino acids | Number of residues |
|---|---|
| Asn/Asp | 5 |
| Gln/Glu | 10 |
| Ser | 3 |
| Thr | 1 |
| Gly | 5 |
| Ala | 24 |
| Pro | 3 |
| Val | 1 |
| Leu | 1 |
| Ile | 1 |
| Lys | 7 |
| Unknown | ? |

The amino acid composition of LPXTGase was determined by the Rockefeller University Protein Chemistry Laboratory.

We claim:

1. An isolated, glycosylated endopeptidase enzyme, wherein said enzyme is isolated from a *Streptococcus* or a *Staphylococcus* bacterium, has a pH optimum between 7.5 and 10, having no cysteine, methionine or aromatic residues, an apparent molecular weight of 14,000 Da, wherein the endopeptidase cleaves cell surface protein virulence factors of said bacterium which contains a Leu Pro Xaa Thr Glu (SEQ ID NO: 1; LPXTG) motif, and is capable of cleaving an LPXTG substrate peptide SEQ ID NO:2 after the serine at position 6 and after the glutamic acid at position 9 to generate peptide fragments TGETANPFY (SEQ ID NO:7) and TANPFY (SEQ ID NO:6) respectively, and wherein the glycosyl carbohydrates are L-fucose, D-galactosamine, D-glucose, D-glucosamine, and D-mannose which are linked to the polypeptide backbone of said endopeptidase are essential for enzyme activity.

2. The enzyme of claim 1, wherein the *Streptococcus* is *Streptococcus pyogenes* or the *Staphylococcus* is *Staphylococcus aureus*.

3. The enzyme of claim 2, wherein the enzyme is further characterized as being inhibited by hydroxylamine at a concentration of about 100 mM, as having a backbone structure containing about 30% unknown amino acids and as having a Km of 0.26 mM when its substrate comprises the amino acid sequence of SEQ ID NO: 2.

4. A screening method for identifying agents capable of inhibiting the endopeptidase enzyme of claim 1 that cleaves at the Leu Pro Xaa Thr Glu (LPXTG) motif (LPXTGase), comprising:
   (a) preparing a radioactively labeled LPXTG motif peptide substrate;
   (b) attaching the radioactive peptide substrate to a solid support;
   (c) contacting the endopeptidase of claim 1 with the peptide substrate on the solid support in the presence or absence of a test compound under conditions which allow cleavage of the substrate; and
   (d) determining release of radioactivity,
wherein an agent capable of inhibiting LPXTGase activity is identified when the release of radioactivity is inhibited or decreased in the presence but not the absence of the agent.

5. The enzyme of claim 1, wherein the virulence factor of the *Streptococcus* bacterium is an M protein.

6. The enzyme of claim 5, wherein the M protein is the M6 protein from *Streptococcus pyogenes*.

7. An isolated glycosylated enzyme isolated from a *Streptococcus* bacterium or a *Staphylococcus* bacterium, wherein the enzyme has the following characteristics:
   a) a pH optimum between 7.5 and 10;
   b) an apparent molecular weight of 14,000 Daltons;
   c) having no cysteine or methionine residues;
   d) having no aromatic amino acid residues;
   e) being inhibited by hydroxylamine at a concentration of about 100 mM;
   f) having a backbone structure containing about 30% unknown amino acids;
   g) having a Km of 0.26 mM when its substrate comprises the amino acid sequence of SEQ ID NO: 2;
   h) cleaving a substrate containing an amino acid sequence comprising a LeuProXaaThrGlu (SEQ ID NO: 1; LPXTG) motif; wherein said substrate comprises the amino acid sequence of SEQ ID NO: 2, and wherein the enzyme cleaves after the serine at position 6 and after the glutamic acid at position 9 to generate peptide fragments TGETANPFY (SEQ ID NO:7 and TANPFY (SEQ ID NO:6) respectively; and
   (i) wherein the glycosyl carbohydrates L-fucose, D-galactosamine, D-glucose, D-glucosamine, and D-mannose which are linked to the polypeptide backbone of said enzyme are essential for enzyme activity.

* * * * *